United States Patent
Kaigala et al.

(10) Patent No.: US 11,515,009 B2
(45) Date of Patent: Nov. 29, 2022

(54) BIOMARKER QUANTIFICATION IN A TISSUE SAMPLE

(71) Applicant: International Business Machines Corporation, Armonk, NY (US)

(72) Inventors: Govind Kaigala, Rueschlikon (CH); Anna Fomitcheva Khartchenko, Zurich (CH); Aditya Kashyap, Zurich (CH); Maria Gabrani, Thalwil (CH); Pushpak Pati, Zurich (CH)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1291 days.

(21) Appl. No.: 15/924,745

(22) Filed: Mar. 19, 2018

(65) Prior Publication Data
US 2019/0286790 A1    Sep. 19, 2019

(51) Int. Cl.
*G16B 40/00*    (2019.01)
*G16H 50/30*    (2018.01)
*G06V 20/69*    (2022.01)

(52) U.S. Cl.
CPC .......... *G16B 40/00* (2019.02); *G06V 20/698* (2022.01); *G16H 50/30* (2018.01); *G01N 2800/50* (2013.01); *G01N 2800/60* (2013.01); *G06T 2207/30004* (2013.01)

(58) Field of Classification Search
None
See application file for complete search history.

(56) References Cited

U.S. PATENT DOCUMENTS

| | | |
|---|---|---|
| 8,559,693 B2 | 10/2013 | Macaulay et al. |
| 9,298,968 B1 | 3/2016 | Peljto et al. |

FOREIGN PATENT DOCUMENTS

| | | | | |
|---|---|---|---|---|
| DE | 102020113000 A1 | * | 11/2021 | |
| JP | 2022023912 A | * | 2/2022 | ............ G06K 9/0014 |
| JP | 7047059 B2 | * | 4/2022 | ......... G01N 15/1475 |
| WO | 2002086498 A1 | | 10/2002 | |
| WO | 2015191978 A1 | | 12/2015 | |
| WO | 2017137422 A1 | | 8/2017 | |

OTHER PUBLICATIONS

Lovchik et al. (Lab on a Chip (2012) vol. 12: Supplementary Material pp. 1-8.*
Ciftik et al. PNAS (2013) vol. 110:5363-5368.*
Hartig Current Protocols in Molecular Biology (2013) vol. 14:12 pages.*
Kashyap et al. Nature Biomedical Engineering (2019) vol. 3:478-490.*
Autebert et al., "Hierarchical Hydrodynamic Flow Confinement: Efficient Use and Retrieval of Chemicals for Microscale Chemistry on Surfaces," Langmuir 30.12, 2014, pp. 3640-3645.
Camp et al., "Automated subcellular localization and quantification of protein expression in tissue microarrays," Nature Medicine 8.11, 2002, pp. 1323-1328.
Cors et al., "Tissue lithography: Microscale dewaxing to enable retrospective studies on formalin-fixed paraffin-embedded (FFPE) tissue sections," PLoS One 12.5, May 2017, 14 pages.
Horner, "Staining tissue samples at the microscale," Lab on a Chip Blog, http://blogs.rsc.org/lc/2012/01/12/staining-tissue-samples-at-the-microscale/ (electronically retrieved Sep. 20, 2017), 3 pages.
Kaigala et al., "A Vertical Microfluidic Probe," Langmuir 27.9, 2011, pp. 5686-5693.
Kwon et al., "Automated Measurement of Multiple Cancer Biomarkers Using Quantum-Dot-Based Microfluidic Immunohistochemistry," Analytical Chemistry 87.8, 2015, pp. 4177-4183.
Lab on a Chip, vol. 12, Issue 6, 2012, pp. 997-1192, http://pubs.rsc.org/en/journals/journalissues/lc#!issueid=lc012006&type=current&issnprint=1473-0197 (retrieved Mar. 13, 2018).
Lovchik et al., "Micro-immunohistochemistry using a microfluidic probe," Lab on a Chip, vol. 12, No. 6, 2012, pp. 1040-1043.
Matkowskyj et al., "Quantitative Immunohistochemistry by Measuring Cumulative Signal Strength Accurately Measures Receptor Number," Journal of Histochemistry & Cytochemistry 51.2, 2003, pp. 205-214.
Rizzardi et al., "Quantitative comparison of immunohistochemical staining measured by digital image analysis versus pathologist visual scoring," Diagnostic Pathology 7.1, 2012, 10 pages.
Robinson, J. Paul, "Principles of Confocal Microscopy," Methods in Cell Biology, vol. 63, Part A, 2001, pp. 89-106.
Shaw, Peter, "Deconvolution in 3-D optical microscopy," The Histochemical Journal 26.9, 1994, pp. 687-694.

* cited by examiner

*Primary Examiner* — Lori A. Clow
(74) *Attorney, Agent, or Firm* — Cantor Colburn LLP; Daniel Morris

(57) ABSTRACT

Embodiments of the invention relate to a computer-implemented method for quantifying a biomarker in a tissue sample of an organism. An image analysis system receives images of a stained tissue sample. Each received digital image depicts the tissue sample region at the end of an exposure interval. The system analyzes the intensity values and exposure intervals of the received digital images for determining the time when the intensity values corresponding to the plurality of exposure intervals ordered according to ascending exposure interval lengths reach a plateau (saturation residence time—SRT). The system determines the amount of a biomarker in the tissue sample and/or predicts a tumor stage and/or a treatment recommendation as a function of the SRT.

18 Claims, 8 Drawing Sheets

Time 1 < Time 2 < Time 3
Longitudinal studies to investigate the evolution of SRT with time

BIOMARKER QUANTIFICATION IN A TISSUE SAMPLE

BACKGROUND

The present invention relates to the field of tissue analysis, and more specifically, to systems and methods for biomarker quantification.

Known tissue analysis approaches like tissue microarray technology offers the opportunity for high throughput analysis of tissue samples for identifying and validating drug targets and/or prognostic markers (e.g. estrogen receptor (ER) and HER2/neu) and candidate therapeutics. Automated quantitative analysis of tissue samples, however, presents several challenges: tissue sections are often highly heterogeneous in respect to tissue morphology, subcellular localization of staining, and the signal to noise ratio. Depending on the type of tumor or tissue section being analyzed, the area of interest may represent nearly the entire sample, or only a small percentage.

In order to roughly estimate the expression level of a given marker in the whole tissue sample, the tissue sample or parts thereof may be stained and the signal strength used as an indicator of the expression level. For example, some methods based e.g. on confocal and convolution/ deconvolution microscopy have been proposed to quantify expression of proteins at the cellular (or sub-cellular) level within a single high power field.

However, these approaches have several drawbacks: they are computationally intensive and laborious techniques; the antibodies and detection systems are expensive; and the light intensity signal in the images acquired in the sample depends on numerous dependencies ranging from the illumination strength of the light source, protocol parameters of the staining procedure (e.g. temperature, incubation time, composition of washing solution, etc.), the sensitivity of the image acquisition system and others. Often, if DAB is used as a stain, the signal intensity may be weak, because DAB is a light scatterer and doesn't follow Lambert-Beer law. Moreover, once the intensity of the signal received by the image acquisition system from the tissue sample reaches or exceeds a saturation level, it is impossible to distinguish differences in the amount of the biomarker based on the signal strength. Thus, biomarker quantification based on the signal strength of the stain as currently used tends to be expensive, inaccurate, subjective and limited in scope.

SUMMARY

In one aspect of the invention, embodiments of the invention relate to a computer-implemented method for quantifying a biomarker in a tissue sample of an organism. The method includes receiving, by an image analysis system, a plurality of digital images of the tissue sample. The tissue sample is stained with a stain. The intensity values in each of the received digital images correlate with the amount of stain directly or indirectly bound to or colocalized with the biomarker in a region of the tissue sample depicted in said digital image. Each received digital image has assigned an exposure interval. Each of the received digital images depicts the tissue sample or the tissue sample regions at the end of said exposure interval. Each exposure interval is a time interval in which a direct binder is in contact with and is able to bind the biomarker. For example, the exposure interval can be the time interval between applying the direct binder on the region of the tissue sample and the time of acquiring the respective digital image. According to other examples, the exposure interval is the time interval between applying the direct binder on the region of the tissue sample and the time of stopping the binding reaction, e.g. by applying a stopping solution. The substance is the stain or a substance that mediates indirect binding or colocalization of the stain to the biomarker. The method further includes analyzing, by the image analysis system, the intensity values and exposure intervals of the received digital images for determining a saturation residence time (SRT). The SRT is the time when the intensity values of the tissue sample regions ordered according to ascending exposure interval lengths reach or approach a plateau. The method further includes determining, by the image analysis system, the amount of the biomarker in the tissue sample of the organism as a function of the SRT. In addition, or alternatively, the method includes predicting, by the image analysis system, a tumor stage and/or a treatment recommendation as a function of the SRT.

According to embodiments, a µIHC staining system is used for staining the tissue sample. The µIHC staining system includes a microfluidic probe head (MFP head) and a control logic configured to control the MFP head such that the MFP head creates a plurality of dots on a single tissue sample or in each of a plurality of adjacent tissue samples. The dots are generated by applying one or more fluids selectively on adjacent regions of the sample to form one of the dots. One of the one or more fluids includes the direct binder. The region of the tissue sample depicted in each of the received digital images depicting or including one of the dots. The image analysis system is configured to analyze the intensity values of the images for determining the SRT selectively in regions of the digital image depicting one of the dots or sub-regions thereof.

According to embodiments, the dots are microscale footprints.

According to embodiments of the invention, each of the dots includes at least a first confinement including a primary antibody acting as the direct binder. The secondary antibody mediates indirect binding of the stain to the biomarker or mediates the colocalization of the stain with the biomarker. The method includes globally applying, after the plurality of dots were generated, a solution with the secondary antibody on the sample such that the dots are covered by the secondary antibody solution completely. The method further includes globally applying, after the solution with the secondary antibodies, a staining solution on the sample such that the dots are covered by the staining solution completely. The image analysis system is configured to selectively analyze the intensity values pixels depicting the first confinements within the one or more dots for determining the SRT.

According to embodiments of the invention, each of the dots includes at least a first confinement including a primary antibody acting as the direct binder and including at least a further confinement including a secondary antibody. The secondary antibody mediates indirect binding of the stain to the biomarker or mediates the colocalization of the stain with the biomarker. The method includes globally applying, after the plurality of dots were generated, a solution with the secondary antibody on the sample such that the dots are covered by the secondary antibody solution completely. The method further includes globally applying, after the solution with the secondary antibodies, a staining solution on the sample such that the dots are covered by the staining solution completely. The image analysis system is configured to selectively analyze the intensity values pixels depicting the first confinements within the one or more dots for determining the SRT and is configured to use the intensity values of image regions depicting one or more of further ones of the confinements as control.

In a further aspect, the invention relates to a tangible computer-readable storage medium including computer-interpretable instructions which, when executed by a processor, causes the processor to perform the image analysis and/or MFP head control steps in accordance with the method described herein for embodiments of the invention.

In a further aspect of the invention, embodiments of the invention relate to an image analysis system configured for quantifying a biomarker in a tissue sample of an organism. The image analysis system includes a first interface adapted for receiving a plurality of digital images of the tissue sample. The tissue sample is stained with a stain. The intensity values in each of the received digital images with the amount of stain directly or indirectly bound to or colocalized with the biomarker in a region of the tissue sample depicted in said digital image. Each received digital image has assigned an exposure interval. Each of the received digital images depicts its respective region of the tissue sample at the end of said exposure interval. Each exposure interval is a time interval in which a direct binder is in contact with and is able to bind the biomarker. The substance is the stain or a substance that mediates indirect binding or colocalization of the stain to the biomarker. The image analysis system includes one or more processors configured for analyzing the intensity values and exposure intervals of the received digital images for determining a saturation residence time (SRT). The SRT is the time when the intensity values of the plurality of received digital images ordered according to ascending exposure interval lengths reach a plateau. The one or more processors are further configured for determining the amount of the biomarker in the tissue sample of the organism as a function of the SRT and/or predicting a tumor stage and/or a treatment recommendation as a function of the SRT. The image analysis system further includes a second interface adapted for outputting the amount of biomarker. In addition, or alternatively, the second interface is adapted for outputting the predicted tumor stage and/or the treatment recommendation.

In a further aspect of the invention, embodiments of the invention relate to a system including the image analysis system and a control logic of a µIHC staining system. The control logic is configured to control an MFP head of the µIHC staining system such that the MFP head applies one or more fluids selectively on a plurality of dots in the tissue sample. One of the one or more fluids includes the stain. The image analysis system is configured to analyze the intensity values of the images for determining the SRT selectively in regions of the digital images depicting one of the dots or sub-regions thereof.

BRIEF DESCRIPTION OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure.

In the following embodiments of the invention are explained in greater detail, by way of example only, making reference to the drawings in which.

DETAILED DESCRIPTION

Figure 1A:
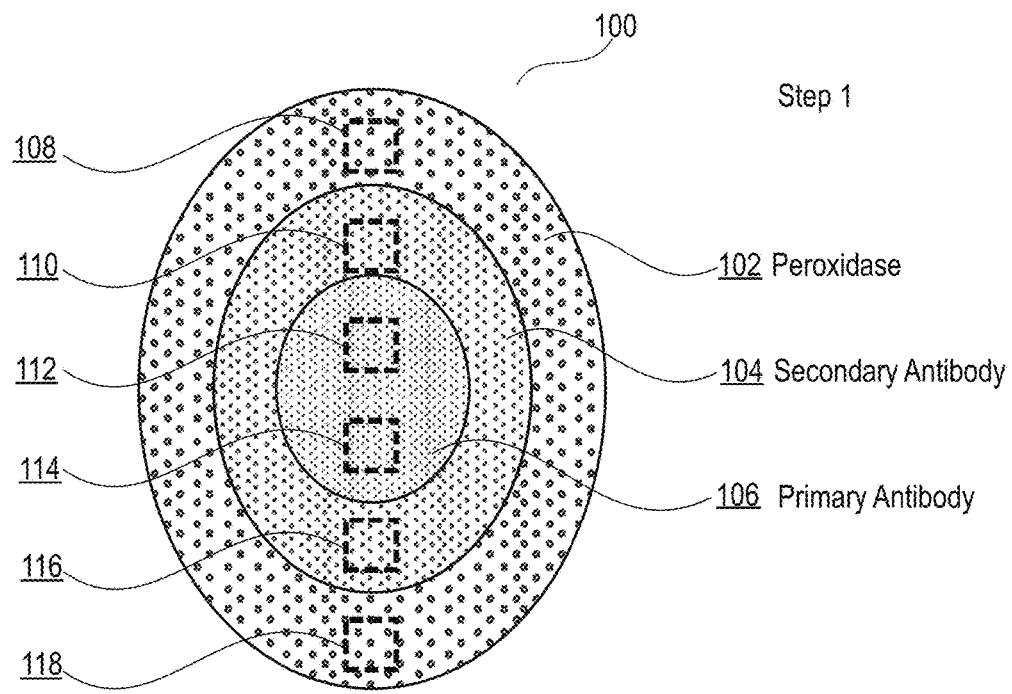
FIGS. 1A-1F depict a multi-step staining procedure using an MFP head and a dot with multiple confinements.

Embodiments of the invention assess the amount of a biomarker based on the kinetics of a staining process, not on an absolute intensity value of a signal generated by the stain. This may be advantageous as this approach may be much more accurate and robust against many sources of error. For example, significant differences in the strength of a staining signal and the corresponding pixel intensity of an image may result from different sensitivities of the camera, and other factors. To the contrary, the rate of the stain binding directly or indirectly to a biomarker and the time when no significant increase of the staining signal can be measured due to a saturation of the biomarker molecules is largely independent of said factors or at least less dependent on them as approaches which try to quantify a biomarker based on a signal strength alone.

Using MFP heads for generating multiple dots on a tissue sample may be particularly advantageous in this context, because the amount of stain and other reagents necessary for measuring the signal strength of a stained sample at the end of multiple different exposure intervals may greatly be reduced. Moreover, the use of MFP technology may allow determining the SRT using many dots on a sample and even in many adjacent tissue slices, thereby allowing a 3D visualization of the SRT-based assessed amount of a particular biomarker. In a still further beneficial aspect, using MFP technology in this context may allow the generation of dots with multiple confinements, whereby one or more of said confinements can include liquids to be used as controls. Thus, embodiments of the invention may allow using many local controls when determining the SRT for particular regions (dots) of a tissue sample, thereby increasing the accuracy of biomarker quantification. Undesired side effects like unspecific bindings of the primary and secondary antibody may be caused or modulated by local factors such as the permeability of the tissue for the various solutions used in a staining protocol, so the use of local controls provided by confined regions generated by an MFP head may allow comparing the intensity value obtained in each confinement of a dot where a "standard" staining protocol was applied with the intensity values obtained in one or more other confinements used as a control.

An "exposure interval" as used herein is a time interval in which a direct binder is in contact with and is able to bind the biomarker in a tissue sample or in a region of the tissue sample. For example, the exposure interval can be the time interval between applying the direct binder on the tissue sample or the region of the tissue sample and the time of acquiring the respective digital image. According to other examples, the exposure interval is the time interval between applying the direct binder on the tissue sample or the region of the tissue sample and the time of stopping the binding reaction, e.g. by applying a stopping solution. Said direct binder is the stain or a substance that mediates indirect binding of the stain to the biomarker or colocalization of the stain with the biomarker. For example, an enzymatic reaction that triggers the generation of a light signal or a color change selectively in the region of the sample where this enzymatic reaction takes place results in a colocalization of the stain with the biomarker provided that the enzyme is colocalized with or directly or indirectly bound to the biomarker. The exposure intervals of a plurality of images may differ from each other because they have a different starting time of applying the direct binder on the tissue sample and/or because they have a different image acquisition times. In some embodiments, each received digital image depicts one or more regions which are selectively incubated in a plurality of solutions in accordance with a staining protocol. Said regions are also referred herein as "dots". Each dot can have associated a respective exposure interval. In case an image depicts multiple dots, an image can have assigned multiple exposure intervals, whereby each exposure interval is assigned to a respective one of the dots in this image. The direct binder can be a stain, e.g. a primary antibody already linked to a chromophore, or a substance that mediates indirect binding or colocalization of the stain to the biomarker.

A "stain" as used herein can be any molecule that generates or modulates electromagnetic light such that a signal being indicative of this light or its modulation be captured and represented as pixel intensity value by an image acquisition signal. The stain may be adapted to generate the signal alone or in response to an interaction with a further molecule or a physical trigger, e.g. light emitted by a light source. The stain can be an IHC stain, in particular a stain adapted for bright field microscopy, or a fluorescent stain.

A "direct binder" as used herein is a substance that directly and preferably selectively binds to another substance, e.g. by an ionic or non-covalent bond. The other substance is typically a biomarker, e.g. a particular protein.

An "indirect binder" as used herein is a substance that does not directly bind to a particular other substance, e.g. a biomarker, but binds to another substance (referred herein as intermediate substance) that directly or indirectly (via one or more further intermediate substances) binds to said particular other substance.

According to embodiments, the determination of the biomarker in the tissue sample includes comparing, by the image analysis system, the determined SRT for a given tissue sample with a plurality of reference SRTs. Each reference SRT is stored in association with an empirically determined amount of biomarker in a reference tissue sample, the reference tissue sample having been stained with the same stain and preferably in accordance with the same staining protocol. The image analysis system is configured to identify the one of the reference SRTs being the most similar to the determined SRT. Then, the image analysis system outputs the amount of biomarker stored in association with the identified reference SRT as the determined amount of the biomarker in the tissue sample of the organism.

The reference SRT may have been determined empirically in a plurality of preliminary tests with a set of reference tissues of interest. For example, if the tissue sample to be analyzed is a liver biopsy of a cancer patient, a plurality of liver biopsies of other patients with known amount of the biomarker of interest may be stained and analyzed as described above for determining the SRT times for the respective reference tissue samples. Then, by comparing the SRT of the currently examined sample with the reference SRTs, embodiments of the invention allow assessing the amount of the biomarker of interest by comparing the SRT obtained for the currently examined tissue sample with the reference SRT times. Thus, according to embodiments of the invention, an accurate absolute quantification of the amount of a biomarker of interest is provided based on reference tissue samples with known amounts of said biomarker. For example, mass spectrometry, HPLC and other techniques may be used for quantifying a particular protein in a tissue samples. Typically, existing methods allowing an absolute quantification of a particular biomolecules are too expensive and complicated to allow for their use in a high-throughput diagnostic laboratory. Here, these expensive methods need to be applied only once on a limited set of reference samples for providing the reference SRTs and respective biomarker amount values. All other steps like determining the SRT for a currently examined sample and comparing this SRT with existing reference SRT values can be performed quickly and fully automatically by an image analysis system.

According to some embodiments, relative quantification of two or more biomarkers, e.g. two or more tumor markers, is performed using a chromogen system (e.g. DAB). This method can be used in pathology labs and provides for an easily analyzable signal. The choice of concentration of the primary antibody together with its SRT can be used as a method for selecting the dynamic range of interest of the primary antibody concentration for the analysis of a certain protein. According to embodiments, quantification of biomarkers is performed by determining absolute amount values, e.g. by using fluorescence stains. Fluorescent signal can be obtained by adding a fluorophore molecule or a quantum dot to the primary or secondary antibody used for detection. The intensity obtained through a fluorescence signal can be correlated with number of proteins per area using a reference curve, which can be generated on a model system (e.g. cell-blocks, antibody patterned slides) that provides a reference tissue sample. Using fluorescence stains may allow analyzing saturation curves for different proteins (multiplexing).

According to other embodiments, the amount of the biomarker of interest in the reference tissue samples is not known, but other attributes of relevance may be known, e.g. the disease progression of the patient from which the reference tissue sample was derived, drugs and treatment schemes which proved effective or non-effective in said patient, and the like. Thus, the reference tissues and the respectively obtained reference SRTs may serve to characterize a tumor from a patient even in case the absolute amount of the biomarker in the sample is not known, e.g. by means of using tumor tissue samples of other patient with a known patient history as a reference, thus aiding in choosing a treatment modality.

According to embodiments, the tissue sample is stained with at least one further stain. For example, the stain mentioned above may directly or indirectly bind to a first biomarker, e.g. Her2, and the further stain may directly or indirectly bind to a second biomarker, e.g. p53. Preferably, each stain used for staining a respective biomarker in the tissue sample is adapted to generate a light signal that has a different spectrum than the light signal emitted by all other stains. For each of one or more further biomarkers contained in or expected to be contained in the tissue sample and for which a respective stain was applied on the sample, the method includes: receiving, by the image analysis system, a plurality of further digital images of the tissue sample. The intensity values in each of the further received digital images correlating with the amount of further stain directly or indirectly bound to or colocalized with said further biomarker in the region of the tissue sample depicted in said further digital image. Each received further digital image has assigned an exposure interval. In some examples, each of the received further digital images depicts the tissue sample or the tissue sample region at the end of said further exposure interval. Each further exposure interval is a time interval in which a further direct binder is in contact with and is able to bind the further biomarker in the tissue sample or in the region of the tissue sample. The further direct binder is the further stain that selectively stains the further biomarker or is a further substance that mediates indirect binding or colocalization of the further stain to the further biomarker. The image analysis system analyzes the intensity values and exposure intervals of the further received digital images for determining a further saturation residence time (SRT). The further SRT is the time when the intensity values of the plurality of further received digital images ordered according to ascending exposure interval lengths reaches a plateau. The image analysis system compares the determined further SRT with a plurality of further reference SRTs. Each further reference SRT is stored in association with an empirically determined amount of the further biomarker in a reference tissue having been stained with the further stain and preferably in accordance with the same staining protocol used for staining the further biomarker in the tissue sample depicted by the further received images. Then, the image analysis system identifies the one of the further reference SRTs being the most similar to the determined further SRT. Then, the image analysis system outputs the amount of further biomarker stored in association with the identified further reference SRT as the determined amount of the further biomarker in the tissue sample of the organism.

This may be advantageous for multiple reasons: by determining a respective SRT for two or more different biomarkers using different types of direct or indirect stains, a multi-dimensional SRT profile of a patient or of a tissue sample of a patient can be obtained. The multi-dimensional SRT profile as depicted, for example, in FIG. 11, may allow a better characterization of the tissue and optionally also of the disease of the patient than a single SRT of a single biomarker. A multi-dimensional SRT profile may allow providing a more accurate description of the current state of a tumor or other type of tissue and/or may allow providing a more accurate prediction of disease progression than a single SRT for a single SRT value.

According to embodiments, two different types of stains may be used for staining the same biomarker and for quantifying the amount of this biomarker based on two different SRT values obtained from the light signals emitted by the two stains respectively. This may increase the accuracy of biomarker quantification.

For example, multiple different IHC stains can be used for staining different biomarkers, whereby for each of the different stains, a plurality of images with different exposure intervals are acquired with the same camera settings.

According to embodiments, the reference tissue sample from which the plurality of reference SRT (and further reference SRT, if any) were empirically determined, include healthy tissue, primary tumor tissue, and metastatic tumor tissue. The method further includes classifying, by the image analysis system, the tissue sample of the organism into one of three tissue types including healthy tissue, primary tumor tissue and metastatic tumor tissue. The classification is performed as a function of the SRT (and each of the one or more further SRT, if any). The image analysis system is configured to output the result of the classification, e.g. via a printer or a screen or any other output means.

Figure 10:
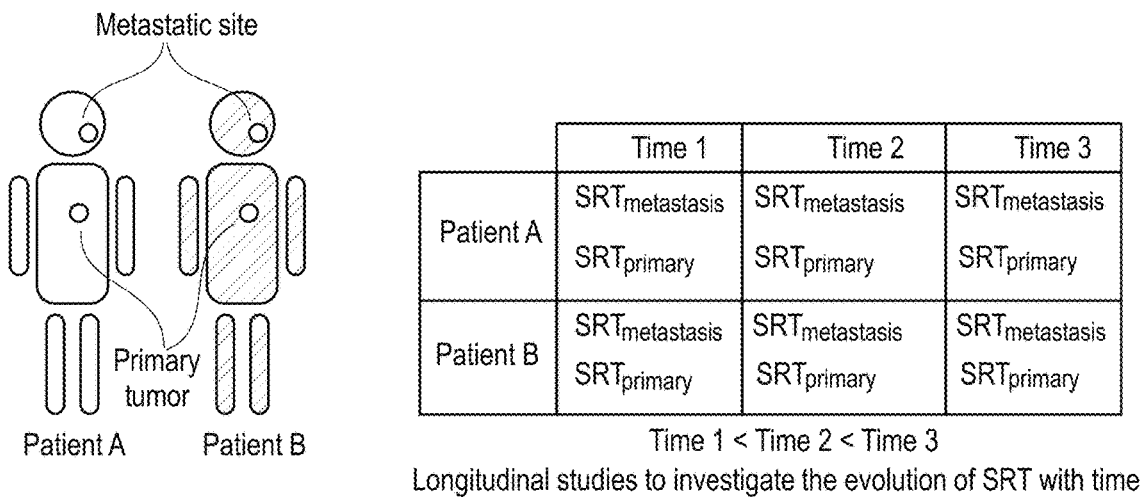
FIG. 10 depicts results of SRT based longitudinal studies.

For example, in longitudinal studies as depicted in FIG. 10, the SRTs of different tissue types may be obtained over a long time interval, e.g. multiple month, from a plurality of patients. By comparing the SRT time obtained in a particular primary or metastatic tumor tissue with an SRT profile obtained for the same tissue type in other patients, it may be possible to determine if a particular drug should be used for treating the patient by taking into account the effectiveness of this drug having been observed in the patients whose SRT profile in the respective tissue type is similar to the SRT of the currently examined tissue sample. It has been observed that the SRT may not only depend on the tissue type (e.g. lung. liver, brain, etc.) of the patient where a tumor is located, but also on the question whether the tissue sample represents primary tumor tissue or metastatic tumor tissue.

According to embodiments, the reference tissue samples and/or the further reference tissue samples are one of: tissue samples derived from the organism and from the same tissue from which the tissue sample was derived; or tissue samples derived from another organism of the same species as the organism, the tissue sample of the other organism having the same tissue type as the tissue sample; or a cell block generated from cell culture cells of the same or a related species as the organism, the cell culture cells having the same tissue type as the tissue sample. For example, the cell block can be a paraffin embedded cell block.

The type of tissue used for generating the reference SRTs may depend on the particular biomedical question examined.

According to embodiments, the method further includes generating the plurality of reference times and the plurality of further reference times, if any. The generation of the reference times includes: providing one or more reference tissue samples; controlling, by the control logic of µIHC staining system, the MFP head such that the MFP head applies one or more fluids selectively on the plurality of dots in each of the reference tissue samples, one of the one or more fluids including the stain; for example, the MFP head can be configured to apply a primary antibody and incubate it for a predefined first time interval; then, a secondary antibody and optionally one or more further intermediary substances and a stain are applied on the same tissue sample globally, e.g. with a pipette, whereby between each application of a fluid by the MFP head and/or by the pipette a predefined, protocol-specific incubation time is awaited for establishing the binding of the stain or any intermediary substance to the biomarker; said or another image analysis system receives a plurality of reference digital images. The reference digital images depict the one or more reference tissue samples or sub-regions thereof. The reference tissue sample is stained with the same type of stain as the tissue sample. The intensity values in the reference digital images correlate with the amount of stain directly or indirectly bound to the biomarker in the reference tissue sample. According to some examples, each of the reference digital images depicts the reference tissue sample or regions thereof at the end of an exposure interval. The exposure interval is a time interval in which a direct binder is in contact with and is able to bind the biomarker in the reference tissue sample or in a region of the reference tissue sample. Then, said image analysis system analyzes the intensity values and exposure intervals of the received digital reference images for determining one or more reference SRTs, each reference SRT being the time when the intensity values of reference digital images having been ordered according to ascending exposure interval lengths and depicting the same reference tissue sample and/or the same region thereof reach a plateau. Then, the amount of the biomarker in each sub-region of each of the reference tissue samples for which a reference SRT was determined is empirically determined, e.g. by means of mass spectroscopy, etc. Then, the image analysis system stores the determined reference SRT in association with the amount of the biomarker having been empirically determined for the reference tissue sample or region thereof for which the reference SRT was determined. Preferably, the reference SRTs are stored also in association with the staining protocol, e.g. stain type, biomarker type, stain concentration, stain type biomarker, buffer, temperature, etc.

Said features may be advantageous as the generation of tissue type specific or even tissue-type and patient-type specific reference SRT values may further increase the accuracy of SRT based biomarker quantification and/or prognosis.

According to some embodiments, the determining of the SRT is performed for each one of the dots by interpolating the image intensity values at said dot captured by an image acquisition system at the end of multiple different exposure intervals. For example, the stain may be a direct binder, e.g. a primary antibody directly labeled with a fluorescent stain. In this case, the stain can be applied by the MFP head or by a pipette on the tissue sample at a particular starting time t0. Then, after each of a plurality of exposure intervals, e.g. in the range of 0.1-120 seconds, e.g. every 30 seconds, an image is taken. Thus, a plurality of images with different exposure times are generated which depict the same dot at different times. The intensity values of this dot may be plotted as depicted in FIG. 7A and interpolated for obtaining the SRT value at a particular time for this tissue sample or sub-region thereof.

According to other embodiments, the determining of the SRT is performed for all dots in the tissue sample or the ROI collectively by interpolating the image intensity values of said dots, whereby the image acquisition system can take a single image of all the dots, but all the dots in the tissue or ROI may have different time intervals between applying the direct binder and the indirect binder with the stain. For example, the stain can be a direct binder as described above, or an indirect binder, e.g. DAB that is oxidized and generates a brown color signal if oxidized by the intermediate substance streptavidin-peroxidase that can selectively bind to a biotinylated secondary antibody used as further intermediary substance.

According to embodiments, the prediction of the tumor stage and/or of the treatment recommendation includes computing, by the image analysis system, the predicted tumor stage as a function of the SRT (and each of the one or more further SRT, if any). In addition, or alternatively, the image analysis system computes the treatment recommendation as a function of the SRT (and each of the one or more further SRTs, if any). The computing of the treatment recommendation can include applying an SRT based classifier, e.g. a trained neural network or support vector machine, on the one or more SRTs (and further SRTs, if any). The image analysis system outputs the predicted tumor stage and/or the treatment recommendation via a man-machine interface, e.g. a screen or a printer.

According to embodiments, the region of the tissue sample depicted in each of the received digital images is or include one of a plurality of dots. The staining of the tissue sample is performed by an µIHC staining system including a microfluidic probe head (MFP head) and a control logic. The control logic is configured such that it causes the MFP head to generate the plurality of dots on a single tissue sample or in each of a plurality of (preferably adjacent or spatially closely connected) tissue samples by applying one or more fluids selectively on adjacent regions of the sample to form one of the dots. Thereby, one of the one or more fluids includes the direct binder. The image analysis system is configured to perform the analysis of the intensity values of the images for determining the SRT selectively in regions of the digital image depicting one of the dots or sub-regions thereof (e.g. in the one of a plurality of confinements that include the direct binder).

Using an MFP head in this context may be highly advantageous as already very small amounts of staining solution and antibodies are sufficient for obtaining multiple, region-specific SRTs for one or even multiple adjacent tissue slices, thereby providing the data basis for a 2D or even 3D visualization of the biomarker concentration obtained from the SRT values of the plurality of dots in the tissue sample(s).

Direct Binders Used as Stains

According to embodiments, the direct binder is the stain. A direct binder as used herein is a substance adapted to selectively and directly bind to the biomarker. In particular, the direct binder can be a primary antibody coupled to a fluorophore or chromophore. The primary antibody is adapted to directly and selectively bind to the biomarker of interest.

Using direct binders as stains may be advantageous as the staining protocol is accelerated and facilitated. Moreover, a single dot may be sufficient for obtaining an SRT value for a tissue or tissue region, because multiple images can be obtained from the same dot after different exposure intervals starting from the same starting time. Thus, simple kinetics based on a continuous monitoring of a single dot may be sufficient for obtaining an SRT value.

According to embodiments, the method includes generating (e.g. with an MFP head or with a pipette), one or more liquid dots on the tissue sample or on a region of interest (ROI) of the tissue sample. Each dot includes a staining solution with the stain. Then, the image acquisition system acquires, for each of the one or more dots, a plurality of images depicting said dot. Each of the plurality of images acquired for a dot depicts said dot at different time intervals since the liquid dot was generated by applying the dot on the tissue sample. The time intervals represent exposure intervals. The plurality of images and the respective exposure intervals acquired for each of the one or more dots are provided to the image analysis system for use as the received plurality of digital images. Then, the image analysis system determines the SRT for each one of the one or more generated liquid dots by interpolating the intensity values obtained at the end of multiple different exposure intervals at said one liquid dot. The first one of the received digital images having been used for the interpolation is an image having being acquired immediately (e.g. within 60 seconds or sooner) after the MFP head has applied said liquid dot (the direct binder acting as stain) on the tissue sample. The first one of the received images has assigned the shortest exposure interval. For example, the camera of an image acquisition system may continuously capture images of a single dot, or of multiple dots in a ROI, or of multiple dots in a whole slide image.

In some embodiments, multiple liquid dots are generated also in case the stain is a direct binder. The generation of each liquid dot includes applying the one or more fluids on each of the tissue sample regions where said liquid dot is to be generated such that all dots include the same particular amount of stain. The method may include computing a final, average SRT for all dots in the tissue sample or all dots in the ROI]

Indirect Binders Used as Stains

According to embodiments, the direct binder is not a stain, but rather a substance that mediates indirect binding of the stain to the biomarker or that mediates the colocalization of the stain with the biomarker. Thus, the direct binder mediates the detection of the biomarker via the stain by causing the stain via direct or indirect interactions to selectively accumulate in spatial proximity of the biomarker, i.e., "indirectly" stain the biomarker.

An indirect binder as used herein is a substance adapted to bind to one of one or more intermediate substances, the one or more intermediate substances being adapted to bind to each other, to the indirect binder and to the biomarker such that the indirect binder selectively and indirectly binds the biomarker. In particular, an indirect binder can be a fluorophore or chromophore that binds to and/or reacts with one of the intermediate substances, thereby or permanently generating a light signal or selectively modifying the color of regions of the sample to which the stain has bound.

For example, the direct binder can be a primary antibody that must be bound to a secondary antibody which again must then be incubated in a staining solution for generating a staining signal selectively in tissue regions to which the primary antibody bound to. The stain that finally binds to or colocalized with the direct binder via one or more intermediate substances can be a fluorescent stain may be used as stain which emits fluorescent light and a bright field stain like e.g. DAB may be used as a stain that modifies the color of the tissue regions to which it binds.

The one or more intermediate substances can include, in particular, a secondary antibody and optional enzymes, e.g. peroxidases. The stain, e.g. DAB, is in particular adapted to be coupled via the secondary antibody (and optionally, further intermediate substances such as biotin and strepatavidin-peroxidase, to the direct binder. Said direct binder can be, for example, a primary antibody.

According to preferred embodiments, the primary antibody is applied via an MFP head while all other intermediary substances and the non-direct binding stain, e.g. DAB, are applied globally on the sample or ROI, e.g. via a pipette.

Using indirect binders as stains may be beneficial because they allow decoupling the task of visualizing a biomarker from the particular nature of the biomarker. For example, commercially available kits for staining primary antibodies of a particular species are available that can be used for detecting the primary antibody without having to chemically couple the chromogen to an expensive, biomarker specific primary antibody.

According to embodiments, the exposure time is the time between applying the primary antibody by the MFP head on a confined region of the sample and capturing the image. All intermediates substances are supplied with a substance and staining protocol specific incubation time on all the dots such that all dots have the same incubation time for all the other substances, e.g. a particular immersion time interval tab2 for the second antibody and a particular peroxidase immersion time interval tpx.

This may be advantageous, because the direct binder—typically the primary antibody—is the one of the molecules involved in generating the staining signal that actually binds to the biomarker of interest. Thus, obtaining a binding kinetics of the direct binder by varying the exposure time of the direct binder while keeping the incubation times of all further intermediate substances and the stain constant may allow generating a reproducible SRT time that is more robust against various process parameter variations also in the context of a highly complex staining protocol.

According to embodiments, the method includes generating a plurality liquid dots on the tissue sample or on a region of interest (ROI) of the tissue sample. Each dot includes a solution with a direct binder having been applied on the tissue sample at different times for the different dots. The image acquisition system acquires a plurality of images respectively depicting one of the plurality of dots at the same acquisition time, each of the plurality of images having assigned an exposure interval between direct binder application and image acquisition of different length (this is the result of the different times of applying the direct binder). The method includes providing the plurality of images and the respective exposure intervals to the image analysis system for use as the received plurality of digital images. The image analysis system is configured to determine the SRT for the plurality of generated liquid dots by interpolating the intensity values obtained at the end of multiple different exposure intervals at said plurality of liquid dots. The first one of the received digital images that is used for the interpolation is an image of the last generated one of the plurality of dots, the last generated dot having assigned the shortest exposure interval.

Thus, in the case of the stain being a direct binder, the SRT is preferably obtained by analyzing a plurality of images of the same dot taken at different, subsequent image acquisition times. As the stain is a direct binder, the different exposure times of the images represent the time between applying the direct binder acting as the stain and the image acquisition. The SRT is obtained by interpolating the intensity values observed in the same dot at different, consecutive acquisition times.

In the case of the stain being an indirect binder, the SRT is preferably obtained from a plurality of images of a plurality of different dots based on images taken at the same image acquisition time. The dots are generated by applying a defined amount of the direct binder at different positions on the tissue sample and incubating the direct binder for different times. For example, a MFP head may move with constant velocity over the sample, thereby applying small droplets of a solution including the direct binder, e.g. a primary antibody, on defined positions of the sample. Then, one or more intermediate substances and the stain are globally and sequentially applied on all the spots, whereby the incubation times of the spots with each of the intermediate substances and the stain are identical. Then, a single image is taken from all the spots at an acquisition time and the images may then be computationally split such that sub-images are created respectively depicting only one of the dots. Said sub-images are used as the received images and respectively have assigned a different exposure times, whereby the exposure time of each of the images represents the time between applying the direct binder and the image acquisition.

Confinements

According to embodiments, a plurality of dots are generated on the tissue sample. The dots are generated such that each of the dots includes at least a first confinement including a primary antibody used as the direct binder. After the plurality of dots have been generated, the method includes globally applying a solution with the secondary antibody on the sample such that one or more of the dots are covered by said solutions completely. The method further includes globally applying, after the application of the solution with the secondary antibody, a staining solution on the sample such that the dots are covered by the staining solution completely. For example, a global stain injection unit of an MFP head or a manually or roboter-controlled pipette can be used for globally applying a liquid on a sample or a region of interest (ROI) of the sample. The image analysis system is configured to selectively analyze the intensity values pixels depicting the first confinements within the one or more dots for determining the SRT.

According to embodiments, a plurality of dots are generated on the tissue sample. The dots are generated such that each of the dots includes at least a first confinement including a primary antibody used as the direct binder and includes at least a further confinement including a secondary antibody for mediating the indirect binding or colocalization of the biomarker and the stain. After the plurality of dots have been generated, the method includes globally applying a solution with the secondary antibody on the sample such that one or more of the dots are covered by said solutions completely. The method further includes globally applying, after the application of the solution with the secondary antibody, a staining solution on the sample such that the dots are covered by the staining solution completely. For example, a global stain injection unit of an MFP head or a manually or roboter-controlled pipette can be used for globally applying a liquid on a sample or a region of interest (ROI) of the sample. The image analysis system is configured to selectively analyze the intensity values pixels depicting the first confinements within the one or more dots for determining the SRT and is configured to use the intensity values of image regions depicting one or more of other ones of the confinements as control.

According to embodiments, the generation of each of the dots includes applying, by the MFP head, a defined amount of a first one of a plurality of different fluids on the tissue sample such that the same amount of each one of the fluids is applied selectively in a respective first one of the confinements of each of the dots. The first fluid is a solution of the direct binder. The MFP head in addition applies a defined amount of a second one of a plurality of different fluids on the tissue sample such that the same amount of the second fluid is applied selectively in a respective second one of the confinements of each of the dots. The second fluid is a solution of an intermediate substance mediates the indirect binding of the direct binder and the stain or mediates the colocalization of the direct binder and the stain. The MFP head applies a defined amount of a third one of a plurality of different fluids on the tissue sample such that the same amount of the third fluid is applied selectively in a respective third one of the confinements of each of the dots. The third fluid is a staining solution.

According to embodiments of the invention, a second fluid is a solution with the one of the intermediate substances adapted to directly bind to the intermediate substance of the first fluid. Said second fluid is applied selectively in a second one of the confinements. In particular, the intermediate substance of the second fluid can be a secondary antibody adapted to selectively bind to the primary antibody.

According to embodiments of the invention, a third fluid is a staining solution including the stain (whereby the stain is an indirect binder). Said third fluid is applied selectively in a third one of the confinements. For example, the secondary antibody may be coupled to streptavidin molecules and the stain can be a fluorescence or bright field fluorophore coupled to a biotin molecule.

According to embodiments, the method further including globally applying, after the plurality of dots were generated, a further volume of the second fluid on the sample such that one or more of the dots are covered by said further volume of the second fluid completely. For example, the further volume can be applied by a manually or roboter-controlled pipette or by an MFP head or global stain injection unit. For example, this step can include globally applying a solution with the secondary antibody on the one or more dots. After the further volume of the second fluid was applied, a further volume of the staining solution is globally applied on the sample such that one or more of the dots are covered by said staining solution completely. Thus, all confinements of each of the one or more dots are covered by the further volume of the second fluid and then are covered by a further volume of the staining solution. The image analysis system is configured to analyze the intensity values of the images for determining the SRT selectively in regions of the digital image depicting the first confinement within the one or more dots and to use the intensity values of image regions depicting one or more of other ones of the confinements as control.

For example, the first fluid can be a solution including a primary antibody, the second fluid can be a solution including a secondary antibody and the staining solution can be a chromophore adapted to bind to the secondary antibody.

Further Embodiments

According to embodiments, the first fluid includes a primary antibody adapted to selectively bind to the biomarker. The second fluid includes a secondary antibody adapted to selectively bind to the first antibody.

According to some embodiments, the confinements of each of the dots are created by the MFP head by applying a hierarchical flow of the multiple different liquids concurrently on the region of the sample where the dot is generated.

According to alternative embodiments, the confinements of each of the dots are created by moving the MFP over the sample, thereby coordinating the application of each of the multiple liquids via different openings of the MFP head such that multiple dots having the same composition of the multiple confinements are created.

According to embodiments, the velocity of the movement of the MFP head results in the different exposure intervals of the dots. For example, the MFP control logic can be configured such that it controls the velocity of the movement of the MFP head such that the exposure time differences of the dots sequentially generated by the moving MFP head allow plotting an intensity profile including enough information to determine the SRT for the currently examined biomarker based on an interpolation of the plot. As the binding kinetics may depend on the biomarker currently examined and on the type of direct binder used for directly or indirectly coupling a stain to said biomarker, the control logic may adapt the movement velocity of the MFP head in a biomarker-specific way to ensure the intensity values obtained at the end of the different exposure intervals of the dots allow for an accurate determination of the SRT for said biomarker. For example, in case a primary antibody used as direct binder has only a weak affinity to the biomarker of interest, the intensities of the dots need to be monitored for a longer time span to ensure that also intensity values of the plots next to or within the plateau phase of the intensity signal are covered. In this case, the movement velocity of the head is reduced. In case a primary antibody has a strong binding affinity to the biomarker, the plateau phase of the signal intensity will be reached already after a comparatively short exposure intervals and the velocity of the movement of the MFP head can be increased.

Controlling the exposure intervals via the movement velocity of the MFP head may be advantageous, as an easy way of adapting the exposure interval to the binding kinetics of different biomarkers and direct binders can be provided.

According to embodiments, each of the dots is generated by an MFP head.

According to embodiments, the MFP head includes at least one injection duct for the direct binder and for each of the intermediate substance mediating the binding of or colocalization of the direct binder and the stain. The MFP head further includes a plurality of aspiration ducts. The injection ducts and aspiration ducts are designed and positioned such that the aspiration ducts generate the borders of each of the confinements by aspirating excessive fluids from the surface of the tissue sample and are configured such that the injection ducts selectively inject one of the multiple liquids to a respective one of the confinements.

Figure 5:
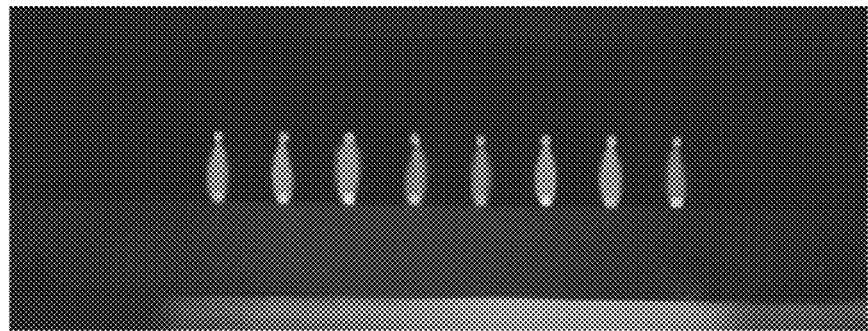
FIG. 5 depicts a plurality of confinements generated by an MFP head using parallel flow.

FIG. 1 depicts a multi-step staining procedure using an MFP head and a dot with multiple confinements. According to embodiments, the MFP head is adapted for precisely applying small volumes of fluids on a sample. For example, the MFP head can be adapted to apply fluids in the sub-milliliter range via micrometer-length scale channels. Volumes well below one nanoliter can be handled and analyzed by fabricating structures with lateral channel dimensions in the micrometer range. Parallel streams (as shown in FIG. 5) or hierarchical streams of liquids (as shown in FIG. 1B) can possibly be accurately and reproducibility controlled, allowing for chemical reactions and gradients to be made at liquid/liquid and liquid/solid interfaces in tightly confined regions of the sample. Typical volumes of fluids in microfluidics range from 10-15 L to 10-5 L and are transported, circulated or more generally moved via microchannels with a typical diameter of 10-7 m to 10-4 m. At the microscale, the behavior of fluids can differ from that at a larger, e.g., macroscopic, scale, such that surface tension, viscous energy dissipation and fluidic resistance may become dominant characteristics of the fluid flow. The Reynolds number, which compares the effects of fluid momentum and viscosity, may decrease to such an extent that liquid flows become laminar rather than turbulent. The absence of turbulence may reduce or prevent the mixing of fluids applied by different MFP head channels, and transport of molecules or small particles between adjacent fluids often takes place through diffusion. As a consequence, certain chemical and physical fluid properties (such as concentration, pH, temperature and shear force) may become deterministic. This makes it possible to obtain more uniform chemical reaction conditions and higher grade products in single and multi-step reactions.

A "microfluidic probe (MFP)" as used herein is a device for depositing, retrieving, transporting, delivering, and/or removing liquids, in particular liquids containing chemical and/or biochemical substances, in the µliter or nano-liter scale. For example, microfluidic probes can be used in the fields of diagnostic medicine, pathology, pharmacology and various branches of analytical chemistry. Microfluidic probes can also be used for performing molecular biology procedures for enzymatic analysis, deoxyribonucleic acid (DNA) analysis and proteomics.

According to embodiment, the MFP head is adapted to change the sizes of the channels and the distance between them, thereby also adapting the size of the generated confinements in a range form few microns (sufficient to cover 2-5 cells) to several hundreds of p.m. This adaptability may be advantageous given the wide range of sizes present in tumors, as well as the extension ranges between different tumor foci.

According to embodiments, a MFP head can be a "vertical MFP head" (also called vertical microfluidic chip) as described, for example, in the literature. The microfluidic probe head includes a body, e.g., a silicon substrate, which has an edge surface forming part of the processing surface of the device. Liquid channels or microchannels are formed at an interface between two layers, by grooving the body up to the edge surface and closing it with a lid, which simplifies the fabrication of the head. In particular, such devices may include a liquid dispenser(s), designed to dispense liquid via an orifice terminating a first one of the channels, and a liquid aspirator(s) aspirates liquid via another orifice and a second one of the channels.

According to embodiments, the MFP head is configured to apply the liquids on the sample such that a hydrodynamic flow confinement (HFC) of the applied liquids is obtained. In some example embodiments, a laminar flow of processing liquid is dispensed from an aperture, which liquid is spatially confined within an environmental liquid (or immersion liquid).

According to embodiments, the confinements ("confined regions") created by an MFP head is created by a hydrodynamic flow confinement (HFC) with a confinement diameter on the order of 100×100 µm2. To process a large area with a HFC, the current approach is to scan over the entire area sequentially. Such a sequential processing is time consuming but may be used, according to embodiments of the invention, for generating dots with one or more liquids having different exposure intervals in respect to at least one of the applied liquids, e.g. in respect to the liquid including a primary antibody. MFP based, dot-wise staining of tissue samples can be performed for immunohistological analysis (detection protein expression levels), detecting ("sensing") protein expression profiles FIG. 1 illustrates a multi-step process of an MFP based IHC staining protocol according to embodiments of the invention, wherein a series of chemicals are sequentially applied to one or more regions ("dots") of a tissue sample. It shows the use of DAB as chromogen in the context of bright field microscopy that provides two controls per dot.

In a first step, the MFP head creates a dot 100 including three concentric confinements as depicted in FIG. 1A. The MFP head selectively applies a first fluid including a primary antibody 106 into the central, circular or ellipsoid confinement, selectively applies a second fluid including a secondary antibody 104 in a second confinement concentrically surrounding the first confinement and applies a third fluid including a chromogen or an intermediate substance, e.g. peroxidase 102, in a third confinement. The confinement borders are preferably arranged such that basically no overlap of the confinement is generated and that the fluids in the different confinements do not mix. Each confinement can be created e.g. by two openings 108-118 in the MFP head. For example, the first confinement with the primary antibody solution can be created by MFP head openings 112 and 114, the second confinement by MFP head openings 110 and 116 and the third confinement by MFP head openings 108 and 118.

Figure 2:
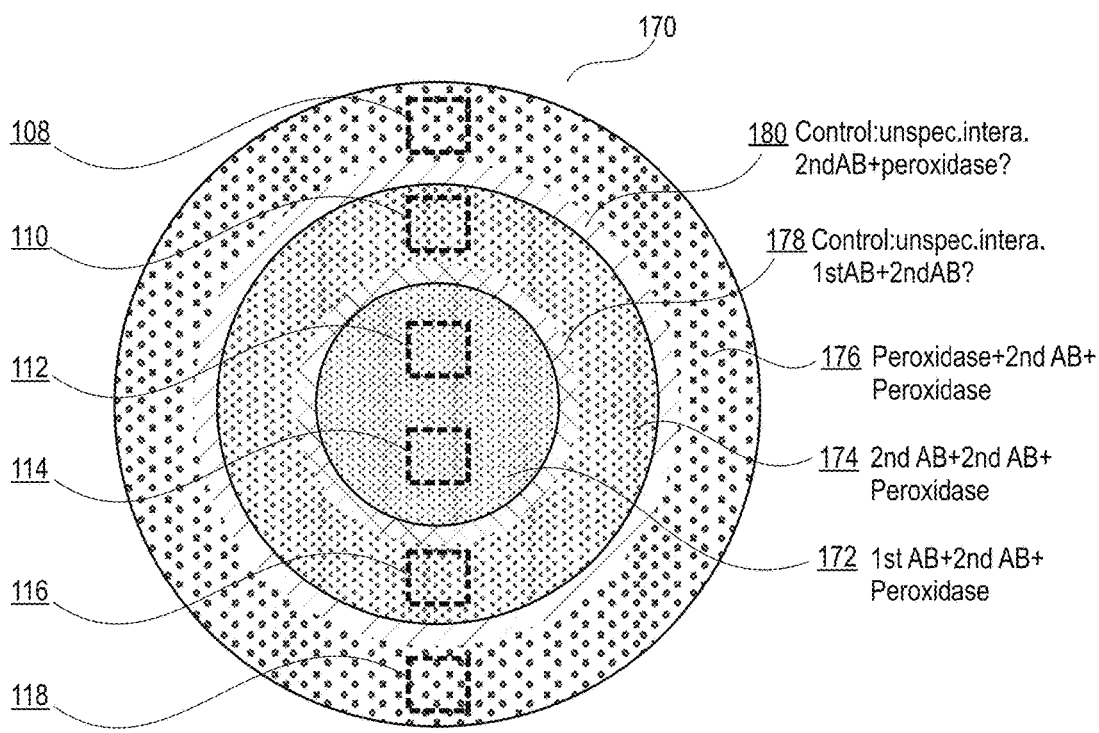
FIG. 2 depicts another dot with multiple confinements.

The dot depicted in FIG. 1A is only one possible example of creating a dot with multiple confinements using a hierarchal HFC. Generating dots with multiple confinements may have the advantage that unspecific background signals can be quantified at the same time as the signal of interest (foreground signal) locally for each of a plurality of tissue regions. For example, the inner confinement can contain the reagent of interest (e.g. the primary antibody), while the outer confinement can contain a secondary reagent which is prone to cause unspecific background (e.g. the secondary antibody). The number of nested confinements can be increased to have several reagents of interest. Information about unspecific binding will provide means towards higher accuracy in quantification. The interface region between the confinements as depicted in FIG. 2 can also give information about any unspecific binding that can cause precipitation on the tissue. Depending on the embodiment, the MFP head can create the multiple confinements using hierarchical flows (FIG. 1A, FIG. 2), parallel flows (FIG. 5) or adjacent flow (not shown).

Figure 1B:
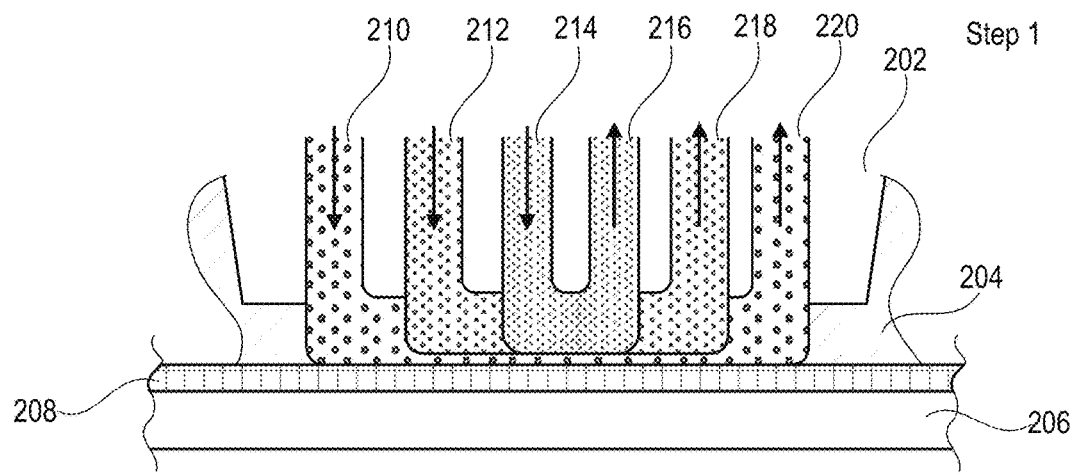

The confinements depicted in FIG. 1A can be created, for example, with an MFP head depicted in FIG. 1B exerting a hierarchical flow control. FIG. 1B shows a slide 206, e.g. a glass slide, including a tissue sample 208 and a MFP head 202 above the tissue sample. The MFP head includes multiple channels, e.g. a channel 214 for applying the first fluid with the primary antibody 106, a channel 216 for soaking up the first fluid, a channel 212 for applying the second fluid with the secondary antibody 104, a channel 218 for soaking up the second fluid, a channel 210 for applying the fluid with the peroxidase 102, and a channel 220 for soaking up the peroxidase fluid. The number of channels and respective confinements is not limited to six channels/three confinements as depicted in FIG. 1A, 1B. In other embodiments, a smaller or larger number of channels for creating a smaller or larger number of confinements may be used. For example, in case only the primary antibody is to be applied with the MFP head without a control, and in case the primary antibody is already coupled to a chromophore ("direct stain"), only channels 214, 216 may be used and the dot 100 may consist of a single confinement. In other embodiments, e.g. when a complex staining protocol is used with additional intermediate substances promoting the indirect binding of the stain and the biomarker, additional channels may be used by the MFP head for creating one or more additional confinements acting as a control. According to some embodiments, the MFP head is configured to apply an immersion liquid 204 to the sample for improving the control of the application of the liquids via the channels of the MFP head. FIG. 1B illustrates the creation of confinements in a dot by a hierarchical flow control: the hierarchy of flow confinements ensure that after steps 1A-1E have been performed, different combinations of the applied chemicals are in contact with the tissue, whereby only one confinement with its respective substance combination is used for measuring a light signal for biomarker quantification and one or more other confinements with their respective substance combinations are used as a control for identifying and eliminating background signals caused by non-specific interactions of the substances.

According to embodiments, the openings (or "orifices") of the MFP head may have respective widths (measured on the edge surface and perpendicular to each of the main surfaces) that, each, lies between 10 µm and 500 µm, and preferably between 20 µm and 200 µm. The MFP head can include the openings in the form of pairs of openings, whereby the openings of each pair or of the whole MFP head may have essentially a same width, to ease the fabrication process and the parametrization of the MFP. According to embodiments, one of the openings of each pair is hydraulically coupled to liquid dispensing unit while the other one of the pair of openings is respectively hydraulically coupled to a liquid aspirator unit, the dispensing and aspiration unit of each pair of opening being jointly designed to make it possible for one of the openings of said pair to aspirate liquid dispensed through the other opening of said pair.

Figure 1C:
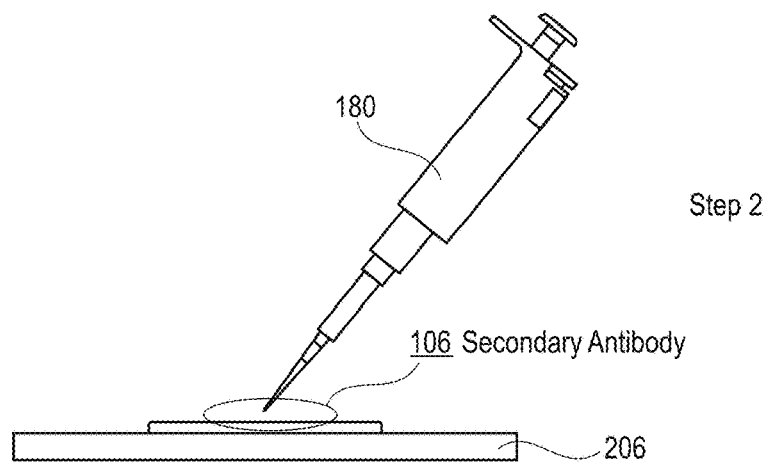

After one or more dots with the multiple confinements as depicted in FIG. 1A have been generated on the tissue sample, a further volume of the second fluid including the secondary antibody is globally applied on all confinements of the one or more dots as depicted in FIG. 1C. For example, a manual or robotic pipette can be used for globally applying the further volume of the second liquid on the tissue sample. The one or more dots can be incubated in the second fluid for a shared predefined incubation time.

Figure 1D:
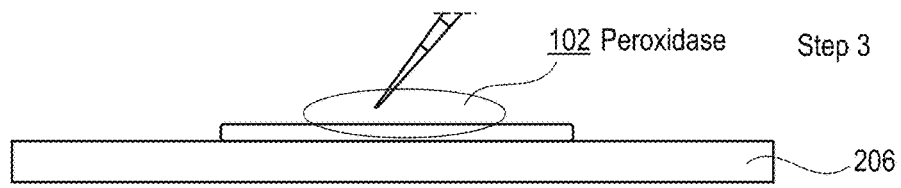

Then, a further volume of the fluid including the peroxidase is globally applied on all confinements of the one or more dots as depicted in FIG. 1D. For example, a manual or robotic pipette can be used for globally applying the peroxidase solution on the tissue sample. The one or more dots can be incubated in the peroxidase solution for a further shared predefined incubation time.

Figure 1E:
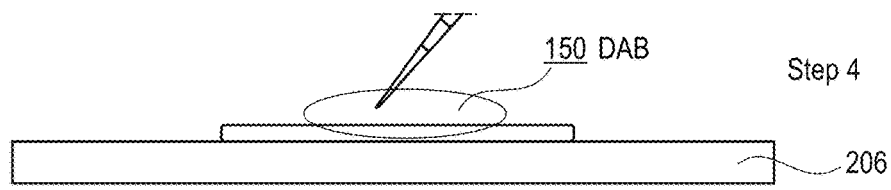

Then, a staining solution, e.g. a DAB (3'-Diaminobenzidine) solution, is globally applied on all confinements of the one or more dots as depicted in FIG. 1E, e.g. by a manual or robotic pipette. The one or more dots can be incubated in the staining solution for a shared predefined staining time.

Figure 1F:
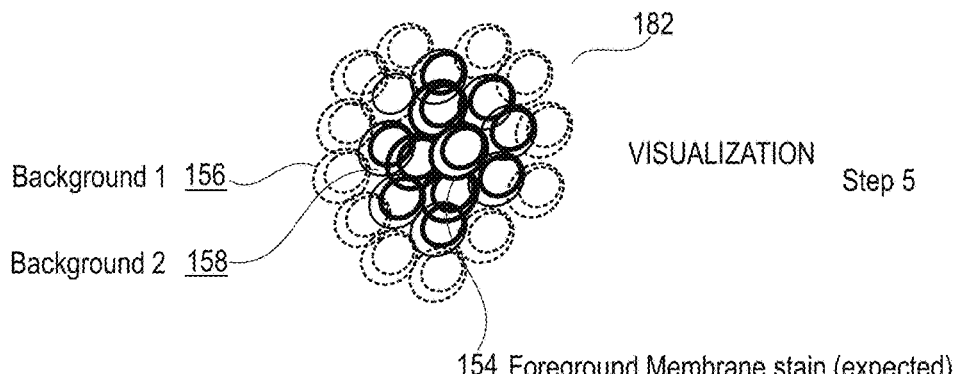

Finally, the signals obtained in the different confinements of each dot can be visualized with an image acquisition system, e.g. a bright field microscope. FIG. 1F depicts a plurality of cells 182 of a tissue region that corresponds to the dot 100 depicted in FIG. 1A. The primary antibody is an antibody that selectively binds to a particular type of cell membrane protein, e.g. a tumor marker.

The four cells at the center of the cell cluster shown in FIG. 1F show the brightest signal that corresponds to the "foreground signal". Only cells within the first confinement are expected to generate the "foreground" signal, i.e. a signal resulting from a selective binding of the stain (DAB) via a plurality of intermediate substances to a biomarker (the membrane protein), because only in the first confinement the complete set of substances for generating the foreground signal was applied: the primary antibody was applied by the MFP head, the secondary antibody, the peroxidase and the stain (DAB) was applied globally in steps 1C-1E.

To the contrary, the eight cells which directly surround the four central cells and which are located within the second confinement (generated by openings 110 and 116) generate a first background signal. The signal obtained from these eight cells is a background (false positive) signal, because the confinement including said eight cells does not include a primary antibody and thus should in theory not generate any signal. However, unspecific interactions between the secondary antibodies 104 applied by the MFP head and the secondary antibodies applied globally in step 1C may result in the generation of the first background signal. According to embodiments, the image analysis system receives the coordinates of the confinement generated by openings 110 and 116 and an indication that this confinement lacks the primary antibody. The image analysis may then use the signal obtained from cells in this confinement for removing the first background signal from all pixels obtained from said sample, including foreground pixels, thereby improving signal quality because background noise generated by an unspecific interaction of the secondary antibodies is removed.

The 12 cells which directly surround the eight "primary background" central cells and which are located within the third confinement (generated by openings 108 and 118) generate a second background signal. The signal obtained from these 12 cells is a background (false positive) signal, because the confinement including said 12 cells neither includes a primary antibody nor a secondary antibody and thus should in theory not generate any signal. However, unspecific interactions between the peroxidase 102 applied by the MFP head and the secondary antibodies applied globally in step 1C may result in the generation of the second background signal. According to embodiments, the image analysis system receives the coordinates of the confinement generated by openings 108 and 118 and an indication that this confinement lacks the primary and secondary antibodies. The image analysis may then use the signal obtained from cells in this confinement for removing the second background signal from all pixels obtained from said sample, including foreground pixels, thereby improving signal quality because background noise generated by an unspecific interaction of the peroxidase and the secondary antibodies is removed.

According to embodiments, only the signal of pixels depicting a confinement onto which all necessary components of a staining protocol have been applied in the correct chronological order are used for determining the SRT and, optionally, determining the amount of the biomarker. The signal obtained from all other confinements is used as a control. This may be beneficial, because for each region of the tissue used for determining the SRT and the SRT-based amount of biomarker, one or more respective, local control signals are obtained. Thus, the signal can be corrected based on local background information. This may be advantageous and may help increasing signal-to-noise ratio, because the strength of the background signal may strongly differ in different regions of the sample, e.g. due to an inhomogeneous distribution of tissue density, stain concentrations, and other factors.

FIG. 2 depicts another dot 170 with multiple confinements and confinement borders generated based on a hierarchical flow control. In contrast to the dot depicted in FIG. 1A, the dot depicted in FIG. 2 includes 5 different confinements respectively corresponding to a different confinement. The additional confinement 178 is created as overlapping region of two other confinements 172, 174, and additional confinement 180 is created as overlapping region of two other confinements 174, 176. The multi-confinement dot 170 is created by controlling the movement and liquid flow of the MFP head such that the applied liquids overlap in defined sub-regions of the dot, thereby creating additional combinations of substances and additional local controls and background signals.

For example, confinement 180 represents a tissue region exposed to a substance combination that will generate a background signal being indicative of an unspecific interaction of the secondary antibody and the peroxidase when both molecule types are present on the surface of the tissue sample at the same time.

Confinement 178 represents a tissue region exposed to a substance combination that will generate a background signal being indicative of an unspecific interaction of the primary antibody and the secondary antibody when both antibody types are present on the surface of the tissue sample at the same time.

Confinement 176 represents a tissue region sequentially exposed to peroxidase, the secondary antibody, peroxidase and DAB and will generate a background signal being indicative of an unspecific interaction of the said substances applied in said sequence on the same tissue region.

Confinement 174 represents a tissue region sequentially exposed to the secondary antibody, the secondary antibody, peroxidase and DAB and will generate a background signal being indicative of an unspecific interaction of the said substances applied in said sequence on the same tissue region.

Confinement 171 represents a tissue region sequentially exposed to the primary antibody, the secondary antibody, peroxidase and DAB and will generate the foreground signal selectively to be used for determining the SRT for the tissue region covered by the dot 170.

Figure 3:
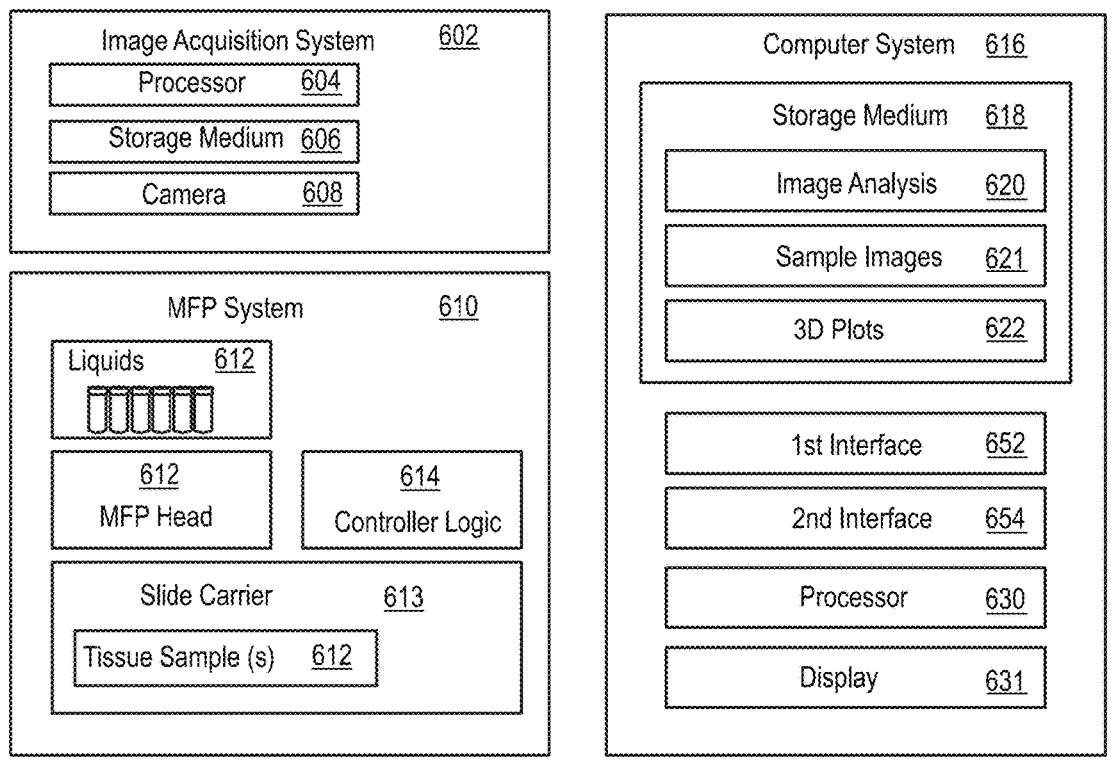
FIG. 3 depicts a block diagram of an image analysis system model layers according to an embodiment of the present invention.

FIG. 3 depicts a block diagram of an image analysis system 616 according to an embodiment of the present invention. The image analysis system can be, for example, a computer system, e.g. a desktop computer system, a server computer, a distributed computer system, e.g. a cloud computer system, or a mobile communication device, e.g. a smartphone. The system 616 includes one or more processors 630, a volatile or non-volatile storage medium 618 and preferably also a display 631. The storage medium includes an image analysis program logic 620. The image analysis logic can be implemented in any kind of software program, e.g. as Java, C, C++ program or the like. In some embodiments, the image analysis logic is configured to receive a plurality of digital images 621 of a tissue sample or of sub-regions (e.g. dots) of a tissue sample, analyze the images and generate various plots 622, e.g. kinetics plots showing the development of an intensity signal indicative of a stained region of the sample, or a 3D visualization of biomarker amounts in the sample. The plots can be displayed to a user via display 631. The images can be received directly from an image acquisition system 602 that can be operatively coupled to the image analysis system, or from any other data source, e.g. a laboratory information system (LIS) or from the storage medium 618.

The image acquisition system 602 that may optionally be coupled to the image analysis system can be, for example, a microscope or a slide scanner. Preferably, the image acquisition system is adapted for high throughput acquisition of images. The image acquisition system can include a camera 608, a volatile or non-volatile storage medium 606 and one or more processors 604 configured for storing the acquired images in the storage medium 606 and/or for forwarding the acquired images to the image analysis system 616.

The image analysis system 602 may optionally be coupled to a microfluidic probe system 610 (MFP system). The MFP system 610 includes one or more MFP heads 612, a plurality of containers 612 with various liquids which are to be applied on a tissue sample via the one or more MFP heads, and a control logic 614 adapted to control the movement of the MFP head, the type and amount of the liquids to be applied on the sample and the time and location of applying the liquids. Optionally, the MFP system can include a slide carrier 613 adapted to carry one or more slides including one or more tissue samples 612.

The system 602 is configured for quantifying a biomarker in a tissue sample of an organism. The system includes a first interface 652 adapted for receiving a plurality of digital images of the tissue sample or of regions of the tissue sample, e.g. from a tissue sample including a plurality of dots created by an MFP head, e.g. a plurality of dots as depicted in FIGS. 1A or 2. For example, the first interface can be a network interface or can be an interface for accessing a storage medium that is internal or external to the image analysis system. Each dot may include at least one sub-region, e.g. a confined region 172, having been stained in accordance with a complete staining protocol such that a signal of this sub-region is expected to correlate with the amount of stained biomarker in the tissue. Optionally, each dot may include one or more further confinements onto which a different composition of the components of a staining protocol were applied, whereby the composition does not include all necessary substances of the respective staining protocol and whereby the confinements onto which said "incomplete" compositions were applied may generate a signal that is interpreted as a background signal generated by an unspecific interaction of the incomplete substance composition and used as a control when interpreting the signal obtained from the sub-region of the dot having been stained in accordance with a complete staining protocol.

For example, the image analysis system can be configured to selectively interpret the intensity of the staining signal obtained from the central confinement 106 of dot 100 or 172 of dot 170 as foreground signal intensity values correlating with the amount of stain directly or indirectly bound to the biomarker in the tissue sample region depicted in said digital image.

For example, a single dot 100, 170 may be generated by an MFP head and then one or more additional substances required in accordance with a staining protocol are applied globally on the sample or ROI of the sample such that the additional substances cover the single dot. After all necessary substances according to the staining protocol have been applied by the MFP head and by the global dispensing unit and have been allowed to cover the dot for the protocol-specific incubation time, a plurality of images is acquired sequentially from this single dot by an image acquisition system 602. As each of the images shows the dot at a different image capture time, each image of this single dot has a different exposure interval. In case the stain is a direct binder, it may not be necessary to apply any substance globally. Rather, the primary antibody applied by the MFP head may already be coupled to a chromophore.

According to other examples, a plurality of dots (e.g. of the type depicted in FIG. 1A or 2) may be generated by an MFP head on a single tissue sample. The MFP head creates the dots sequentially by moving over the sample with a predefined velocity. Then, after all dots have been created, one or more additional substances required in accordance with a staining protocol are applied globally on the sample or ROI of the sample such that the additional substances cover all dots having been generated on the sample or the ROI. After all necessary substances according to the staining protocol have been applied by the MFP head and by the global dispensing unit and have been allowed to cover the dots for the protocol-specific incubation time, a plurality of images respectively depicting one of the plurality of dots is obtained at the same image acquisition time. For example, a single image of all dots can be acquired that is then divided such that each sub-image depicts one of the dots. As the MFP head created the dots at different dot creation times, the time interval between dot generation and image acquisition and thus also the exposure interval is different for each of the dots. In case the stain is a direct binder, it may not be necessary to apply any substance globally. Rather, the primary antibody applied by the MFP head may already be coupled to a chromophore.

The image acquisition system analyzes the intensity values and exposure intervals of the received digital images for determining a saturation residence time (SRT). In some embodiments, only a particular confinement within each dot is used for determining the SRT for the tissue region where the dot was generated, whereby this particular confinement is the confinement onto which all necessary substances in accordance with a staining protocol have been applied on the tissue sample. For example, the SRT can be determined by ordering the images in accordance with their associated exposure interval lengths, plotting the image intensities observed in the dots (or selected confinements therein) of the different images, and determining the time in the plot when pixel intensity curve created by linear interpolation and optionally also extrapolation reaches a plateau as depicted, for example, in FIG. 7B. Finally, the image analysis system computes the amount of the biomarker in the tissue sample of the organism covered by the dot as a function of the SRT. In addition, or alternatively, the image analysis system predicts a tumor stage and/or a treatment recommendation as a function of the SRT.

The image analysis system includes a second interface, e.g. a display, a speaker or a printer, adapted for outputting the amount of biomarker and/or the predicted tumor stage and/or the treatment recommendation to a user.

Figure 4:
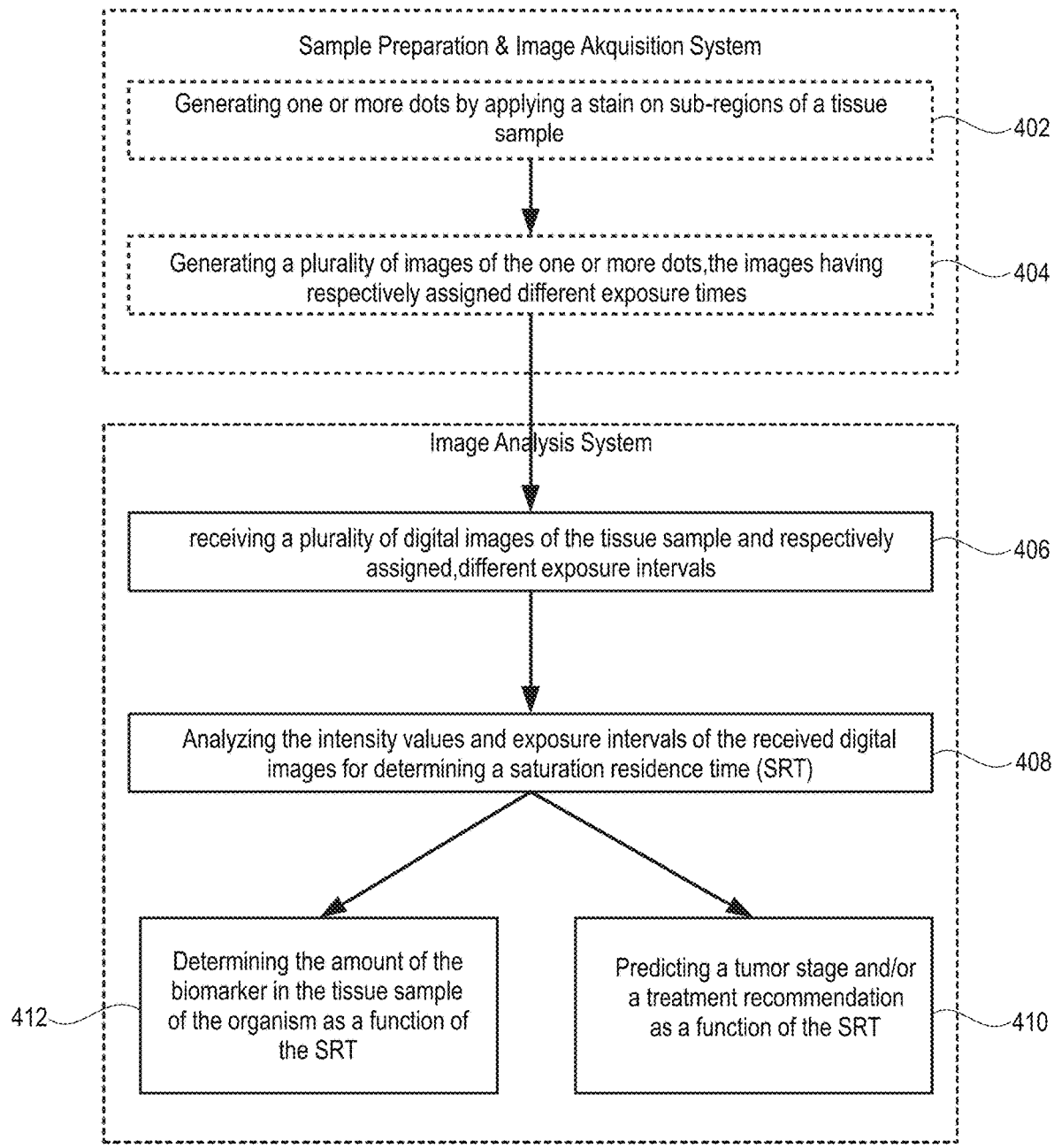
FIG. 4 depicts a flow diagram of a method of determining and using the SRT for biomarker quantification.

FIG. 4 depicts a flow diagram of a method for quantifying a biomarker in a tissue sample of an organism.

Optionally, the method may include some sample preparation and image acquisition steps. For example, a µIHC staining system including a microfluidic probe head (MFP head) may be configured to generate in step 402 one or more dots by applying a stain on sub-regions of a tissue samples as described herein for embodiments of the invention. For example, the stain may be a direct binder and applied in a single step or may be an indirect binder that is applied after applying one or more intermediate substances promoting an indirect binding of the stain and the biomarker of interest. Then in step 404, a plurality of images of the one or more dots are acquired by an image acquisition system, e.g. a camera of a microscope or a slide scanner. The acquired images can be directly forwarded via a network to an image analysis system, e.g. a computer, or can be stored on a non-volatile storage medium used as a physical carrier for providing the images to the image acquisition system. The generation of the images can include splitting a single whole-slide image into multiple sub-images respectively including and displaying one of the dots.

Next in step 406, the image analysis system receives the plurality of digital images of the tissue sample or of regions of the tissue sample. For example, the image analysis system may receive the images directly from an image acquisition system or read the images from a storage medium having stored the images. The tissue sample depicted in the received images has been stained (e.g. in step 402) with a stain. The intensity values of the pixels in each of the received digital images correlate with the amount of stain directly or indirectly bound to the biomarker in the tissue sample depicted in said digital image. Each received digital image has assigned an exposure interval. For example, each of the received digital images depicts the tissue sample or the tissue sample regions (e.g. stained dots in the tissue sample) at the end of said exposure interval. Each exposure interval is a time interval in which a direct binder is in contact with and is able to bind the biomarker in a tissue sample or in a region of the tissue sample, the direct binder being the stain or a substance that mediates indirect binding or colocalization of the stain to the biomarker. For example, the images may depict a plurality of different dots, whereby the stain was applied on the different dots at different starting times of the exposure interval and whereby a single image was taken from all of the dots at the same time. Then, this image was split into multiple sub-images respectively depicting one of the dots, each of the sub-images being used as one of the received images having assigned a different exposure interval due to the difference regarding the time of applying the stain. According to other embodiments, all received images depict the same tissue or the same tissue dot, but were acquired at different moments in time.

Next in step 408, the image analysis system analyzes the intensity values and exposure intervals of the received digital images for determining a saturation residence time (SRT). The SRT is the time when the intensity values of the plurality of received digital images ordered according to ascending exposure interval lengths reach a plateau. Examples for determining the SRTs for two different biomarkers are depicted and described in FIGS. 12 and 13. For example, the determination can be performed by plotting the measured and optionally normalized intensity values of one or more dots in a sample over an exposure time, linearly interpolating and/or linearly extrapolating the plotted values for generating a plot with a connected curve, and determining the time SRT when the intensity value has almost reached the maximum possible (i.e., plateau) value. For example, embodiments of the invention can use the time representing the shortest exposure interval yielding an intensity value that is at least 90% of the maximum intensity value observed in the plot.

Next in step 412, the image analysis system determines the amount of the biomarker in the tissue sample of the organism as a function of the SRT. For example, the method may include comparing the SRT computed in step 408 for a particular tissue or for a particular tissue region (e.g. a dot) with a reference SRT value. The reference SRT value may have been obtained previously for various types of reference tissue.

In addition, or alternatively, the image analysis system in step 410 predicts a tumor stage and/or a treatment recommendation as a function of the SRT. For example, a machine learning program based classifier having been trained on known patient survival times, known tumor stages of various tissues and known SRTs for a set of tumor markers may be used for predicting tumor stage, patient survival and/or appropriate treatment schemes (see e.g. FIG. 8).

FIG. 5 depicts a plurality of confinements generated by an MFP head using parallel flow. The 8 depicted confinements have a teardrop-shape and correspond to 8 parallel flows of a liquid applied by a single MFP head. Depending on the staining protocol used and the number of substances that need to be sequentially applied on the sample in accordance with the staining protocol, the MFP head can be configured to apply more or less than 8 parallel flow confinements. According to one example, the first confinement from the left is a confinement to which a solution of a primary antibody is selectively applied. The second confinement from the left is a confinement to which a solution of a secondary antibody is selectively applied. The third confinement from the left is a confinement to which a peroxidase solution is selectively applied. The fourth confinement from the left is a confinement to which a DAB solution is selectively applied. The control unit of the MFP system may control the movement of the MFP head such that the confinements corresponding to a particular dot are arranged without any overlap but in spatial proximity to each other as depicted in FIG. 1A or with some overlaps as depicted in FIG. 2. The MFP head moves along (scans) the tissue sample such that along the movement trajectory the sample is exposed serially to all the chemicals necessary for staining the sample in accordance with the staining protocol, thereby creating dots. When confinements are generated based on parallel rather than hierarchical flow control, the confinements belonging to the same dot are applied in spatial proximity to each other, e.g. are applied next to each other, but are typically not arranged in a concentric manner. According to embodiments, the velocity of the movement of the MFP head is chosen such that the sample region covered by a particular confinement is immersed in the applied fluid for an incubation interval as specified by the staining protocol.

Figure 6:
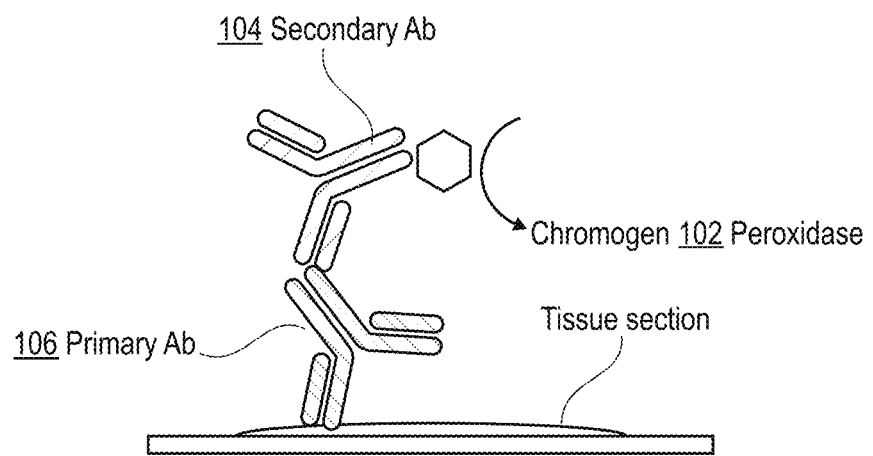
FIG. 6 depicts the binding of a chromogen via a primary and a secondary antibody to a biomarker.

FIG. 6 depicts the binding of a chromogen via a primary and a secondary antibody to a biomarker. The tissue section may be expected to express a particular biomarker, e.g. a tumor marker such as, for example, Her2. According to a particular IHC staining protocol used for staining one or more regions of the tissue sample, the MFP head may apply a first solution including a primary antibody that is adapted to selectively bind to the HER2 protein, if present in the tissues sample. The MFP head may optionally apply further substances in other confined regions of a dot for generating controls. The primary antibody depicted in FIG. 6 acts as a direct binder but is not capable of acting as a stain. Then, a secondary antibody 104 is applied globally on the tissue sample. The secondary antibody is adapted so selectively bind to the primary antibody and thus is expected to selectively bind to regions of the tissue expressing the HER2 biomarker. If the secondary antibody binds to any other region, this is therefore considered to represent a noise signal generated by an unspecific binding of the secondary antibody. Then, a chromogen that actually generates the light signal of the stain is applied, whereby in fact the application of the chromogen may include sequentially or concurrently applying two or more different substances. For example, the secondary antibody can be a biotinylated antibody. Then, a peroxidase coupled to streptavidin is globally applied on the tissue sample. Streptavidin strongly couples the peroxidase to the biotin residues of the secondary antibody, thereby linking the enzymatic function of the peroxidase via two intermediary molecules to the biomarker. Finally, DAB is applied globally. Although DAB is not covalently bound to the biomarker or any of the intermediate substances, the oxidation of DAB to a brown precipitate is performed selectively in regions of the sample including the streptavidin-peroxidase, and thus is performed selectively in regions of the sample expressing the HER2 biomarker.

Figure 7:
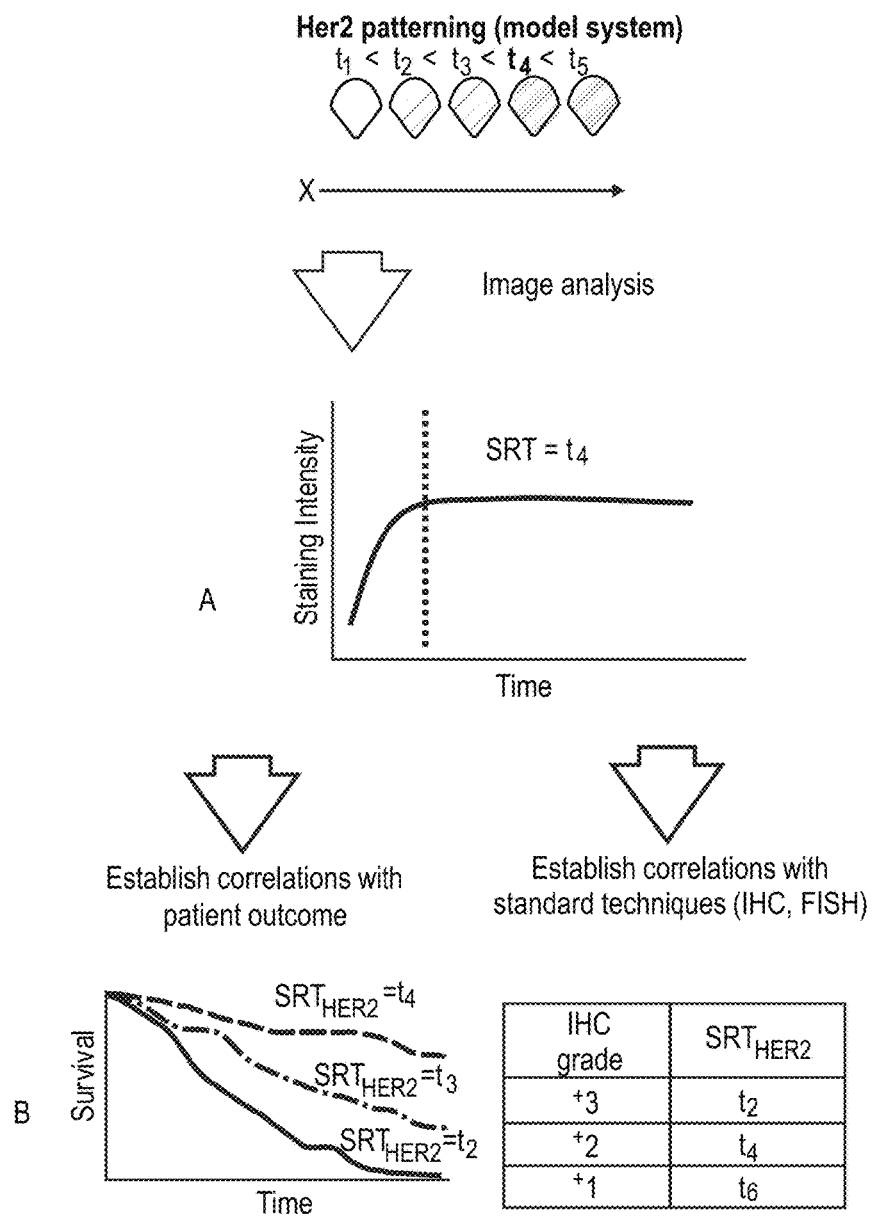
FIG. 7 depicts the identification and use of an SRT in different technical contexts.

FIG. 7 depicts the identification and use of an SRT in different technical contexts. Figure A shows that the MFP heads generates multiple different dots sequentially. At time t1, a first dot is created. For example, the dot can be a dot with one or more confinements as described for FIGS. 1A or 2. Then the MFP head moves further in x-direction and creates at time t2 a further dot and so on until the five dots depicted in FIG. 7A have been created. Then, a single image of the five dots is captured and split into five sub-images respectively depicting one of the five dots. As the dots have different creation times but the same capture time, the exposure interval between creating the dot (applying the first antibody with the MFP head) and the time of image acquisition differs for all dots. Based on an ascending sequence of exposure intervals, the plot depicted in FIG. 7B is computed.

The plot can be generated based on a linear interpolation and optional also extrapolation of the five data value pairs (pixel intensity value—exposure time) obtained for each of the five dots of FIG. 7A. The time when the curve generated by the interpolation and optional extrapolation reaches an intensity plateaus is referred herein as "SRT". According to embodiments, the SRT is the time when the intensity reaches 90% of the maximum intensity value observed in all the dots, a threshold which can be adjusted based on empirical factors. FIGS. 7C and 7D illustrate various statistical and machine-learning based approaches which may use the SRT of multiple different tissue types, patients and respective metadata for predicting patient outcome, drug effectiveness and/or a recommended treatment schema.

SRT can be correlated with conventional IHC grade (for instance, conventional grades for HER2 are 0, +1, +2 and +3) as depicted in FIG. 7C. However, use of SRT values offers higher discretization in the tumor gradation system, which can be chosen by selecting adequate residence times. Moreover, patient outcomes can be correlated with SRT-based levels of protein expression as depicted in FIG. 7B. Comparison of the patient tissue's SRT with well-established cell line SRTs can provide an insight into proper treatment, since drugs are initially tested in cell lines. This can lead to an improvement in personalized therapy and in the use of IHC as a companion in diagnostics. False negative signals will be reduced, since wrong antibody concentration or incubation times will not have an effect on the binding kinetics and thus will not affect the SRT of a particular biomarker. False positive stains could be potentially removed by studying the development of the saturation curve for the foreground pixels and background pixels, whereby background pixels are pixels of one or more confinements per dot which include only a sub-set of reagents used in a staining protocol that should—theoretically—not result in any staining signal but which may in practice generate a background signal as a result of unspecific bindings of two or more of the applied substances.

Figure 8:
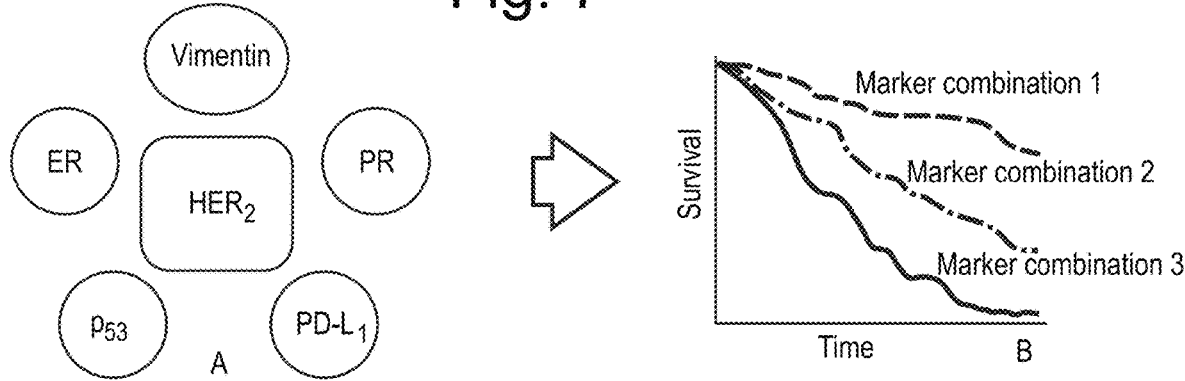
FIG. 8 depicts the prediction of the survival time based on SRTs obtained for different tumor markers.

FIG. 8 depicts the prediction of the survival time based on SRTs obtained for different tumor markers. For example, the SRT for 6 different biomarkers HER2, vimentin, PR, PD-L1, ER and p53 may be determined at first for a plurality of patients and correlated with observed survival times and/or effective treatment modalities. The creation of the correlation can be performed e.g. based on various machine learning approaches, e.g. neural networks or support vector machines, or may simply include defining rule-based heuristics for predicting survival time or a recommended treatment schema based on the observed SRTs for the 6 biomarkers. Then, based on the trained machine learning logic or the heuristics derived from the data obtained from the plurality of patients, the survival time or an effective treatment schema is predicted for a particular patient by determining the SRTs of the 6 biomarkers in a sample of the patient and feeding the obtained 6 SRT values into the trained machine learning logic or the heuristics. Using MFP technology may be particularly advantageous as it allows generating one or more dots for a respective one of a plurality of different staining protocols.

Figure 9:
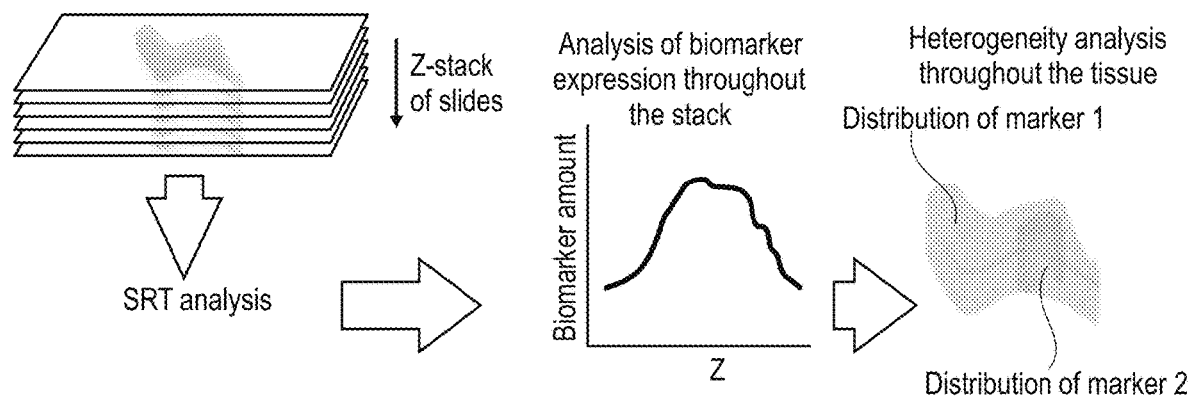
FIG. 9 depicts a 3D visualization of biomarker concentration in a tissue sample.

FIG. 9 depicts a 3D visualization of biomarker concentration in a tissue sample. As was explained already for various embodiments of the invention, the SRT can be used, in combination with one or more reference values, for assessing the amount of a particular biomarker in a tissue based on the SRT obtained for said tissue. In order to perform 3D biomarker quantification, the image acquisition system acquires images of a plurality of adjacent tissue samples of a tissue of an organism. In particular, the one or more adjacent tissue samples can be a z-stack of a plurality of tissue samples that can be provided on a respective slide. The image analysis system receives, for each of the plurality of adjacent tissue samples of a tissue of an organism, one or more digital images depicting multiple different regions of said tissue sample. The image analysis system determines the amount of the biomarker in each of the multiple different regions in the one or more received images as a function of the SRTs determined in said multiple different regions in accordance with the method of biomarker quantification described herein for embodiments of the invention. Then, the image analysis system generates a 3D plot of the plurality of adjacent tissue samples. The intensity of regions within the 3D plot correlates with the amount of the biomarker determined in the respective tissue sample regions. Using MFP technology may be particularly advantageous as it allows determining SRTs for a plurality of different dots in each of a plurality of z-stack slide tissue samples for one or more different biomarkers without consuming an inacceptable large amount of stain or antibody. Thus, a highly accurate 3D quantification of a particular biomarker can be achieved rapidly and at low costs.

Thus the 3D visualization of SRT-based biomarker concentrations may allow evaluating the biomarker distribution throughout a tissue, e.g. a tumor tissue. This would allow to study tumor heterogeneity and the distribution of tumor markers. Moreover, 3D profiles of tumors can be generated, leading to a better understanding of their biology. Infiltration of immune system cells can be visualized with 3D profiles and patterns can be analyzed. By using multiple different fluorescence stains for different biomarkers, it is possible to analyze several biomarkers in the same region.

FIG. 10 depicts results of SRT based longitudinal studies. It was observed that the SRT values obtained for metastatic tissue, primary tumor tissue and healthy tissue showed significant differences. Moreover, it was also shown that the SRT of some biomarkers changed over the time and provided valuable information for predicting the further progression of a disease, e.g. a particular type of cancer, in a patient.

Figure 11:
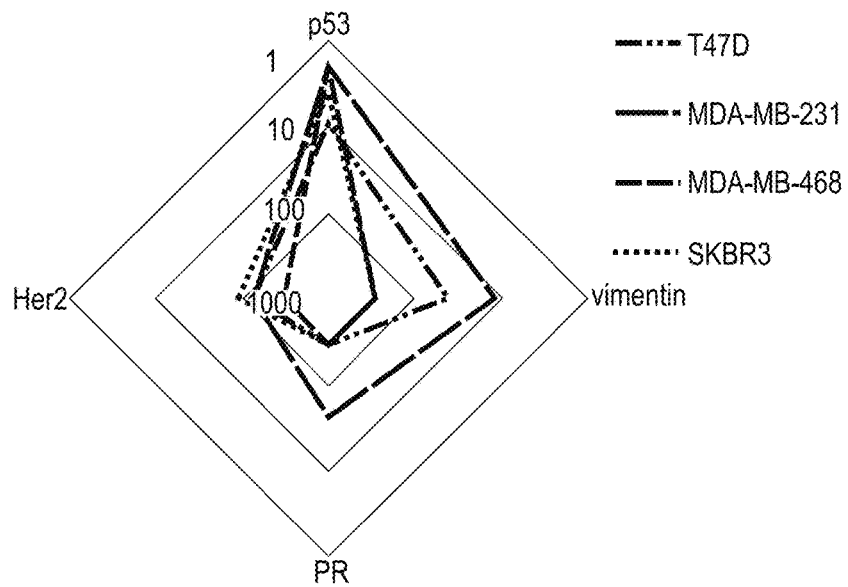
FIG. 11 depicts a profile generated from the SRTs obtained for multiple different biomarkers.

FIG. 11 depicts a spider plot including multiple SRTs obtained for multiple different biomarkers. A particular patient group characterized by a particular, shared survival time or characterized by a particular drug that was proven to be effective in treating a particular disease can be characterized based on a combined SRT profile of multiple biomarker which are characteristic for a particular patient group or for a particular disease or disease state. According to some embodiments, the SRT profile of a predefined set of biomarkers of a patient is determined and used for classifying the patient or the patient's disease and/or for predicting the outcome or progression of a disease or for predicting and recommending a treatment schema.

According to some embodiment, the SRT(s) of one or more respective biomarkers can be examined over time on the same patient to predict the outcome with higher certainty. For example, variations of SRT in epithelial-to-mesenchymal transition (EMT) markers can indicate probability of metastasis. Example markers to be studied are vimentin and SLUG. Tumor invasive fronts can be studied in patients before and after metastatic tumors are found or treatment is applied to analyze variations in EMT markers. A comparison of SRT values for tumor and metastasis present in a patient can give an idea of whether a certain tumor generated that metastasis, and how much time has passed from the moment the metastasis has happened.

Figure 12:
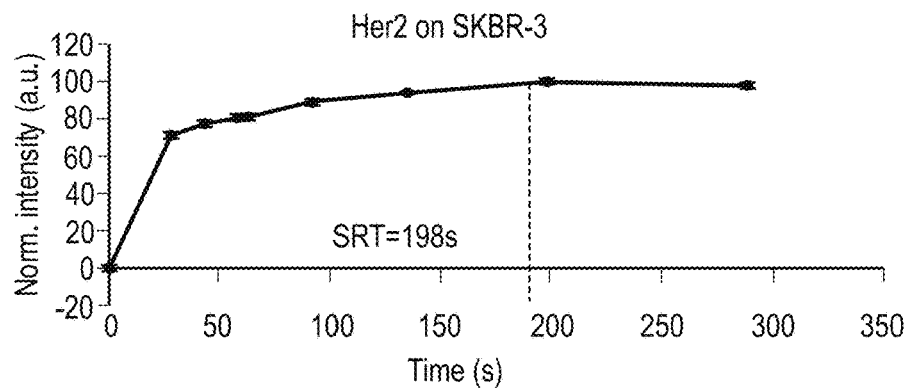
FIG. 12 depicts a signal intensity plot used for computing the SRT of Her2.
Figure 12:
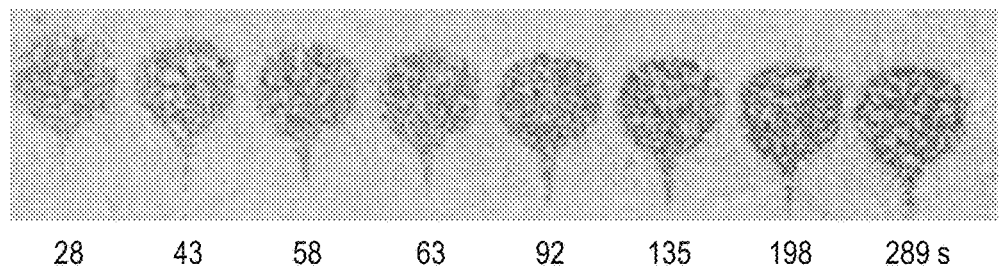

FIG. 12 depicts a signal intensity plot used for computing the SRT of the HER2 biomarker. The image in the lower half of FIG. 12 shows a series of MFP dots with growing exposure times from left to right, whereby the primary antibody of the staining protocol used for generating the multiple dots is adapted to selectively bind to the HER2 protein. The plot in the upper part of FIG. 12 shows a plot with the normalized dot intensity values over the exposure times of the dots depicted below, and the SRT value obtained from this plot for the HER2 biomarker.

Figure 13:
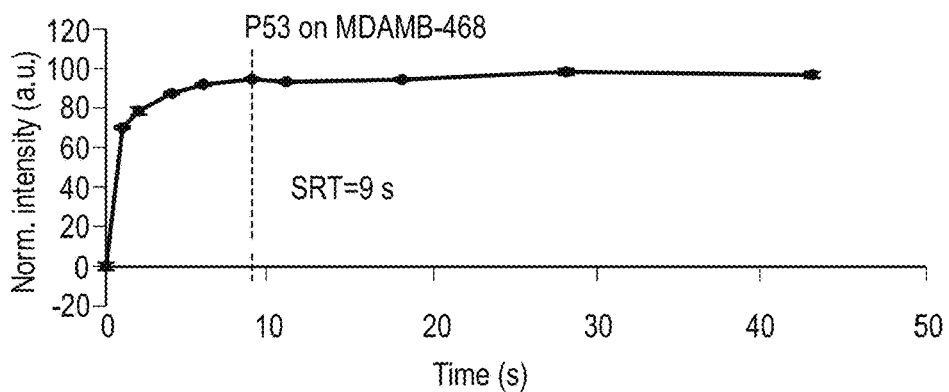
FIG. 13 depicts a signal intensity plot used for computing the SRT of p53.
Figure 13:
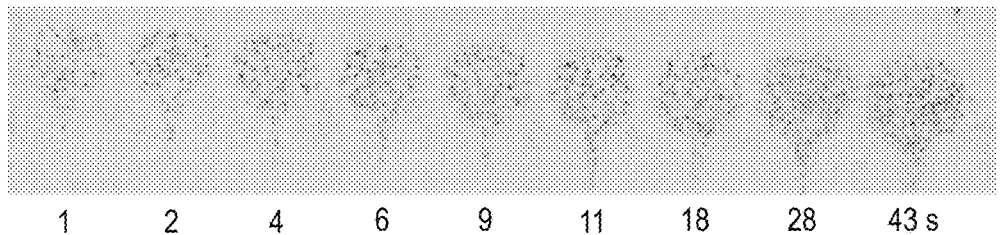

FIG. 13 depicts a signal intensity plot used for computing the SRT of p53. The image in the lower half of FIG. 13 shows a series of MFP dots with growing exposure times from left to right, whereby the primary antibody of the staining protocol used for generating the multiple dots is adapted to selectively bind to the p53 protein. The plot in the upper part of FIG. 13 shows a plot with the normalized dot intensity values over the exposure times of the dots depicted below, and the SRT value obtained from this plot for the p53 biomarker.

Various embodiments are specified in the following numbered clauses.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method for quantifying a biomarker in a tissue sample of an organism, the computer implemented method comprising:
   receiving, by an image analysis system, a plurality of digital images of the tissue sample, the tissue sample being stained with a stain, and wherein intensity values in each of the received digital images correlate with an amount of stain directly or indirectly bound to or colocalized with the biomarker in a region of the tissue sample depicted in said digital image, each received digital image having assigned an exposure interval, each exposure interval being a time interval in which a direct binder is in contact with and is able to bind the biomarker, each of the received digital images depicting a respective region of the tissue sample at the end of said exposure interval, the direct binder being the stain or a substance that mediates indirect binding or colocalization of the stain to the biomarker;
   analyzing, by the image analysis system, the intensity values and exposure intervals of the received digital images, the analyzing comprising:
      ordering the depicted tissue sample regions according to ascending exposure interval lengths; and
      determining a saturation residence time (SRT), the SRT being a time when the intensity values of the ordered depicted tissue sample regions reach a plateau;
   comparing the SRT to at least one reference SRT value; and
   determining, based on the comparison and by the image analysis system, at least one of an amount of the biomarker in the tissue sample of the organism, a predicted tumor stage, and a treatment recommendation.

2. The computer-implemented method of claim 1, further comprising:
   comparing, by the image analysis system, the SRT with a plurality of reference SRTs, each reference SRT being stored in association with an empirically determined amount of biomarker in a reference tissue sample stained with the same stain; and
   outputting, by the image analysis system, the empirically determined amount of biomarker stored in association with the one reference SRT of the reference SRTs having a closest time to the SRT as the determined amount of the biomarker in the tissue sample of the organism.

3. The computer-implemented method of claim 2, further comprising, for each of one or more further biomarkers:
   receiving, by the image analysis system, a plurality of further digital images of the tissue sample, the tissue sample being stained with a further stain, and wherein intensity values in each of the further received digital images correlate with an amount of further stain directly or indirectly bound to or colocalized with said further biomarker in a region of the tissue sample depicted in said further digital image, each received further digital image having assigned a further exposure interval, each of the received further digital images depicting the tissue sample or the tissue sample region at the end of said further exposure interval, each further exposure interval being a time interval in which a further direct binder is in contact with and is able to bind the further biomarker, the further direct binder being the further stain or a substance that mediates indirect binding or colocalization of the further stain to the further biomarker;
   analyzing, by the image analysis system, the intensity values and further exposure intervals of the further received digital images, the analyzing comprising:
      ordering the plurality of received further digital images according to ascending exposure interval lengths; and
      determining a further SRT, the further SRT being a time when the intensity values of the ordered plurality of received further digital images reaches a plateau;
   comparing, by the image analysis system, the determined further SRT with a plurality of further reference SRTs, each further reference SRT being stored in association with an empirically determined amount of the further biomarker in a reference tissue stained with the further stain; and
   outputting, by the image analysis system, the empirically determined amount of further biomarker stored in association with the one further reference SRT of the further reference SRTs having a closest time to the further SRT as the determined amount of the further biomarker in the tissue sample of the organism.

4. The computer-implemented method of claim 3, further comprising generating the plurality of reference SRTs times and the plurality of further reference SRTs, the generation comprising:
  providing one or more reference tissue samples;
  controlling, by a control logic of a micro-immunohistochemistry (μIHC) staining system, a microfluidic probe (MFP) head of the μIHC staining system such that the MFP head applies one or more fluids selectively on a plurality of dots in each of the reference tissue samples, one of the one or more fluids comprising the stain;
  receiving, by said or another image analysis system, a plurality of reference digital images, the reference digital images depicting the one or more reference tissue samples or of regions thereof, the reference tissue sample being stained with the same type of stain as the tissue sample, and wherein intensity values in the reference digital images correlate with an amount of stain directly or indirectly bound to the biomarker in the reference tissue sample, each of the reference digital images depicting the reference tissue sample or regions thereof at the end of an exposure interval, each exposure interval being a time interval in which a direct binder is in contact with and is able to bind the biomarker in the reference tissue sample or regions thereof;
  analyzing, by the image analysis system, the intensity values and exposure intervals of the received digital reference images, the analyzing comprising:
    ordering the reference digital images according to ascending exposure interval lengths; and
    determining one or more reference SRTs, each reference SRT being a time when the intensity values of the ordered reference digital images reach a plateau;
  empirically determining the amount of the biomarker in each region of each of the reference tissue samples for which a reference SRT was determined; and
  storing, by the image analysis system, the determined reference SRT in association with the amount of the biomarker having been empirically determined for the reference tissue sample or region thereof for which the reference SRT was determined.

5. The computer-implemented method of claim 2, wherein the reference tissue sample from which the plurality of reference SRTs are empirically determined comprises: healthy tissue, primary tumor tissue, and metastatic tumor tissue,
  the computer-implemented method further comprising:
  classifying, by the image analysis system, the tissue sample of the organism into one of three tissue types comprising healthy tissue, primary tumor tissue and metastatic tumor tissue, the classification being performed as a function of the SRT; and
  outputting, by the image analysis system, the result of the classification.

6. The computer-implemented method of claim 1, the prediction of the tumor stage and/or of the treatment recommendation comprising:
  computing, by the image analysis system, the predicted tumor stage as a function of the SRT; and/or
  computing, by the image analysis system, the treatment recommendation as a function of the SRT;
  outputting, by the image analysis system, the predicted tumor stage and/or the treatment recommendation via a man-machine interface.

7. The computer-implemented method of claim 1, the region of the tissue sample depicted in each of the received digital images being or comprising one of a plurality of dots, the computer-implemented method further comprising:
  controlling, by a control logic of a μIHC staining system comprising a microfluidic probe head (MFP head), the MFP head such that the MFP head creates the plurality of dots on a single tissue sample or in each of a plurality of tissue samples by applying one or more fluids selectively on adjacent regions of the sample to form one of the dots, one of the one or more fluids comprising the direct binder;
  analyzing, by the image analysis system, the intensity values of the images for determining the SRT selectively as a function of pixel intensity values in regions of the digital image depicting one of the dots or sub-regions thereof.

8. The computer-implemented method of claim 7, each of the dots comprising at least a first confinement comprising a primary antibody used as the direct binder and comprising at least a further confinement comprising a secondary antibody for mediating the indirect binding or colocalization of the biomarker and the stain, the computer-implemented method further comprising:
  after the generation of the plurality of dots, globally applying a solution with the secondary antibody on the sample such that the dots are covered by the secondary antibody solution completely; and
  after the application of the solution with the secondary antibody, globally applying a staining solution on the sample such that the dots are covered by the staining solution completely;
  wherein the analysis of the intensity values further comprises selectively comparing intensity values of pixels depicting the first confinements within the one or more dots against intensity values of control image regions depicting one or more of other ones of the confinements having therein a control liquid as control.

9. The computer-implemented method of claim 8, the confinements of each of the dots being created by the MFP head by applying a hierarchical flow of the multiple different liquids concurrently on the region of the sample where the dot is generated.

10. The computer-implemented method of claim 9, the velocity of the movement of the MFP head resulting in the different exposure intervals of the dots.

11. The computer-implemented method of claim 7, the generation of each of the dots comprising:
  applying, by the MFP head, a defined amount of a first one of a plurality of different fluids on the tissue sample such that the same amount of the first fluid is applied selectively in a respective first one of the confinements of each of the dots, the first fluid being a solution of the direct binder;
  applying, by the MFP head, a defined amount of a second one of a plurality of different fluids on the tissue sample such that the same amount of the second fluid is applied selectively in a respective second one of the confinements of each of the dots, the second fluid being a solution of an intermediate substance mediating the indirect binding of the direct binder and the stain or mediating the colocalization of the direct binder and the stain;
  applying, by the MFP head, a defined amount of a third one of a plurality of different fluids on the tissue sample such that the same amount of the third fluid is applied selectively in a respective third one of the confinements of each of the dots, the third fluid being a staining solution;

the computer-implemented method further comprising:
after the plurality of dots are generated, globally applying a further volume of the second fluid on the sample such that one or more of the dots are covered by said fluid completely; and
after the further volume of the second fluid is applied, globally applying a further volume of the staining solution on the sample such that one or more of the dots are covered by said staining solution completely;
the analyzing of the intensity values of the images for determining the SRT comprising selectively analyzing the intensity values of regions of the digital image depicting the first confinement within the one or more dots and using the intensity values of image regions depicting one or more of other ones of the confinements as control.

12. The computer-implemented method of claim 11, the MFP head comprising at least one injection duct for the direct binder and for each intermediate substance mediating the binding of or colocalization of the direct binder and the stain, the MFP head further comprising a plurality of aspiration ducts, the injection ducts and aspiration ducts being designed and positioned such that the aspiration ducts generate the borders of each of the confinements by aspirating excessive fluids from the surface of the tissue sample and being configured such that the injection ducts selectively inject one of the multiple liquids to a respective one of the confinements.

13. The computer-implemented method of claim 1, the direct binder being the stain, the direct binder being in particular a primary antibody coupled to a chromophore.

14. The computer-implemented method of claim 13, further comprising:
generating one or more liquid dots on the tissue sample or on a region of interest (ROI) of the tissue sample, each dot comprising a solution with the direct binder;
acquiring, by an image acquisition system, for each of the one or more dots, a plurality of images depicting the dot, each of the plurality of images acquired for a dot depicting said dot at different time intervals since the liquid dot was generated, the time intervals representing exposure intervals, and
providing the plurality of images and the respective exposure intervals acquired for each of the one or more dots to the image analysis system for use as the received plurality of digital images;
the image analysis system being configured to determine the SRT for each one of the one or more generated liquid dots by interpolating the intensity values obtained at the end of multiple different exposure intervals at said one liquid dot.

15. The computer-implemented method of claim 14, each of the dots being generated by an MFP head.

16. The computer-implemented method of claim 1, the direct binder being a substance that mediates indirect binding of the stain to the biomarker or that mediates the colocalization of the stain with the biomarker.

17. The computer-implemented method of claim 16, further comprising:
generating a plurality liquid dots on the tissue sample or on a region of interest (ROI) of the tissue sample, each dot comprising a solution with the direct binder, each of the plurality of dots being created at a different time;
acquiring, by an image acquisition system, a plurality of images respectively depicting one of the plurality of dots at the same acquisition time, each of the plurality of images having assigned an exposure interval of different length as a result of the different dot generation times; and
providing the plurality of images and the respective exposure intervals to the image analysis system for use as the received plurality of digital images;
the image analysis system being configured to determine the SRT for the plurality of generated liquid dots by interpolating the intensity values obtained at the end of multiple different exposure intervals at said plurality of liquid dots.

18. A tangible computer-readable storage medium comprising computer-interpretable instructions which, when executed by a processor, causes the processor to perform an image analysis method comprising:
receiving, by an image analysis system, a plurality of digital images of the tissue sample, the tissue sample being stained with a stain, and wherein intensity values in each of the received digital images correlate with an amount of stain directly or indirectly bound to or colocalized with the biomarker in a region of the tissue sample depicted in said digital image, each received digital image having assigned an exposure interval, each exposure interval being a time interval in which a direct binder is in contact with and is able to bind the biomarker, each of the received digital images depicting a its respective region of the tissue sample at the end of said exposure interval, the direct binder being the stain or a substance that mediates indirect binding or colocalization of the stain to the biomarker;
analyzing, by the image analysis system, the intensity values and exposure intervals of the received digital images, the analyzing comprising:
ordering the depicted tissue sample regions according to ascending exposure interval lengths; and
determining a saturation residence time (SRT), the SRT being a time when the intensity values of the ordered depicted tissue sample regions reach a plateau;
comparing the SRT to at least one reference SRT value; and
determining, based on the comparison and by the image analysis system, at least one of an amount of the biomarker in the tissue sample of the organism, a predicted tumor stage, and a treatment recommendation.

* * * * *